United States Patent
Chau et al.

(10) Patent No.: US 9,687,191 B2
(45) Date of Patent: Jun. 27, 2017

(54) METHOD AND DEVICE FOR SWALLOWING IMPAIRMENT DETECTION

(75) Inventors: Thomas T. K. Chau, Toronto (CA); Catriona Steele, Toronto (CA); Ervin Sejdic, London (CA); Bruno C. Maruzzo, Toronto (CA)

(73) Assignees: Holland Bloorview Kids Rehabilitation Hospital, Toronto (CA); University Health Networks, Toronto (CA)

(*) Notice: Subject to any disclaimer, the term of this patent is extended or adjusted under 35 U.S.C. 154(b) by 442 days.

(21) Appl. No.: 13/980,510

(22) PCT Filed: Jan. 18, 2012

(86) PCT No.: PCT/CA2012/000036
§ 371 (c)(1),
(2), (4) Date: Oct. 15, 2013

(87) PCT Pub. No.: WO2012/097436
PCT Pub. Date: Jul. 26, 2012

(65) Prior Publication Data
US 2014/0228714 A1    Aug. 14, 2014

Related U.S. Application Data

(60) Provisional application No. 61/433,450, filed on Jan. 18, 2011.

(51) Int. Cl.
*A61B 5/00* (2006.01)
*A61B 5/11* (2006.01)

(52) U.S. Cl.
CPC .......... *A61B 5/4205* (2013.01); *A61B 5/1121* (2013.01); *A61B 5/1123* (2013.01);
(Continued)

(58) Field of Classification Search
None
See application file for complete search history.

(56) References Cited

U.S. PATENT DOCUMENTS 5,308,326 A * 5/1994 Zimmon ............ A61B 5/02152
604/103.1
6,011,990 A * 1/2000 Schultz ................ A61B 5/0476
600/544
(Continued)

FOREIGN PATENT DOCUMENTS

JP    2008502386    1/2008
WO    2009001449    12/2008

OTHER PUBLICATIONS

MathWorks, "Data Compression using 2D Wavelet Analysis", http://www.mathworks.com/examples/wavelet/646-data-compression-using-2d-wavelet-analysis, May 2, 2007, 8 pages.*
(Continued)

*Primary Examiner* — Devin Henson
*Assistant Examiner* — Matthew Kremer
(74) *Attorney, Agent, or Firm* — K&L Gates LLP

(57) ABSTRACT

A method and an apparatus for swallowing impairment detection acquire dual axis accelerometry data representative of one or more swallowing events executed by a candidate. Upon feature extraction and classification, vibrational data acquired in respect of each swallowing event is classified as indicative of one of normal or possibly impaired swallowing. Computer-readable media comprising statements and instructions for implementation by a processing device are also described in facilitating swallowing impairment detection respective to candidate swallowing events.

33 Claims, 9 Drawing Sheets

(52) U.S. Cl.
CPC ............ *A61B 5/1126* (2013.01); *A61B 5/726* (2013.01); *A61B 5/7267* (2013.01); *A61B 5/7282* (2013.01)

(56) References Cited

U.S. PATENT DOCUMENTS

| | | | | |
|---|---|---|---|---|
| 2001/0020132 | A1* | 9/2001 | Nordstrom | A61B 5/0068 600/476 |
| 2004/0010195 | A1* | 1/2004 | Zelenchuk | A61B 5/0071 600/476 |
| 2004/0249314 | A1* | 12/2004 | Salla | A61B 5/1107 600/595 |
| 2005/0113673 | A1* | 5/2005 | Avinash | A61B 5/055 600/413 |
| 2005/0256414 | A1* | 11/2005 | Kettunen | A61B 5/024 600/509 |
| 2006/0111644 | A1* | 5/2006 | Guttag | A61B 5/048 600/544 |
| 2006/0245631 | A1* | 11/2006 | Levenson | G06K 9/6247 382/133 |
| 2006/0258921 | A1* | 11/2006 | Addison | A61B 5/0002 600/323 |
| 2006/0265022 | A1* | 11/2006 | John | A61N 1/36139 607/45 |
| 2007/0191725 | A1* | 8/2007 | Nelson | A61B 5/0452 600/528 |
| 2007/0238920 | A1* | 10/2007 | Sato | A61B 5/4205 600/102 |
| 2008/0004904 | A1* | 1/2008 | Tran | A61B 5/0006 705/2 |
| 2008/0045804 | A1* | 2/2008 | Williams | A61B 5/112 600/300 |
| 2008/0167569 | A1* | 7/2008 | Ermes | A61B 5/0476 600/544 |
| 2008/0194946 | A1* | 8/2008 | Summers | A61B 5/05 600/425 |
| 2008/0269646 | A1* | 10/2008 | Chau | A61B 5/11 600/595 |
| 2009/0187124 | A1* | 7/2009 | Ludlow | A61H 39/00 601/47 |
| 2009/0275853 | A1* | 11/2009 | Sarkela | A61B 5/04014 600/544 |
| 2010/0160833 | A1* | 6/2010 | Chau | A61B 5/1107 600/593 |
| 2011/0055121 | A1* | 3/2011 | Datta | G06F 19/3418 706/12 |
| 2012/0046641 | A1* | 2/2012 | Jedwab | A61B 5/00 604/503 |

OTHER PUBLICATIONS

Phinyomark, Angkoon, et al., "Optimal Wavelet Functions in Wavelet Denoising for Multifunction Myoelectric Control," ECTI Transactions on Electrical Eng., Electronics, and Communications, vol. 8, No. 1, Feb. 2010, pp. 43-52.*
Tsai, SJS, "Chapter 5 Signal Analysis," http://scholar.lib.vt.edu/theses/available/etd- 12062002-152858/unrestricted/Chapter5.pdf, 2002, pp. 43-79.*
Daggett et al., "Laryngeal Penetration during Deglutition in Normal Subjects of Various Ages", Dysphagia, Oct. 2006, No. 4, at pp. 270-274, vol. 21.
Dusick, "Investigation and management of Dysphagia" Seminars in Pediatric Neurology, 2003, No. 4, pp. 255-264, vol. 10.
Jain et al. "Statistical Pattern Recognition: A Review" IEEE Transactions on Pattern Analysis and Machine Intelligence, Jan. 2000, No. 1, pp. 4-37, vol. 22.
Halper et al. "Dysphagia After Head Trauma: The Effect of Cognitive-Communicative Impairments on Functional Outcomes" Journal of Head Trauma Rehabilitation, Oct. 1999, No. 5, pp. 486,496, vol. 14.
Waito et al., "Voice-Quality Abnormalities as a Sign of Dysphagia: Validation Against Acoustic and Videofluoroscopic Data" Dysphagia, Jun. 2011, No. 2, pp. 125-134, vol. 26.
Efron, "Bootstrap Methods: Another Look at the Jackknife" The Annals of Statistics, 1979, No. 1, pp. 1-26, vol. 7.
Martin-Harris et al. "Clinical Utility of the Modified Barium Swallow" Dysphagia, 2000, No. 1, pp. 136-141, vol. 15.
Martin-Harris et al., "MBS Measurement Tool for Sallow Impairment—MBSImp: Estabilishing a Standard" Dysphagia, Dec. 2008, No. 4, pp. 392-405, vol. 23.
Pelletier et al. "Effect of Citric Acid and Citric Acid-Sucrose Mixtures on Swallowing in Neurogenic Oropharyngeal Dysphagia" Dysphagia, Oct. 2003, No. 4, pp. 231-241, vol. 18.
Borr et al. "Reliability and Validity of Cervical Auscultation" Dysphagia, Jul. 2007, No. 3, pp. 225-234, vol. 22.
Dematteo et al. "Comparison of Clinical and Videofluoroscopic Evaluation of Children with Feeding and Swallowing Difficulties" Developmental Medicine and Child Neurology, Mar. 2005, No. 3, pp. 149-157, vol. 47.
Ertekin et al. "Neurophysiology of Swallowing" Clinical Neurophysiology, Dec. 2003, No. 12, pp. 2226-2244, vol. 114.
Burges "A Tutorial on Support Vector Machines for Pattern Recognition" Data Mining and Knowledge Discovery, Jun. 1998, No. 2, pp. 121-167, vol. 2.
Lazarus et al. "Swallowing Disorders in Closed Head Trauma Patients" Archives of Physical Medicine and Rehabilitation, Feb. 1987, No. 2, pp. 79-84, vol. 68.
Steele et al. "Influence of Bolus Consistency on Lingual Behaviors in Sequential Swallowing" Dysphagia, Aug. 2004, No. 3, pp. 192-206, vol. 19.
Steele et al. "The Relationship Between Hyoid and Laryngeal Displacement and Swallowing Impairment" Clinical Otolaryngology, Feb. 2011, No. 1, pp. 30-36, vol. 36.
Lee et al. "Effects of Liquid Stimuli on Dual-axis Swallowing Accelerometry Signals in a Healthy Population" BioMedical Engineering OnLine, 2010, pp. 1-10, vol. 9.
Cichero et al. "Acoustic Signature of the Normal Swallow: Characterization by Age, Gender, and Bolus Volume" The Annals of Otology, Rhinology & Laryngology, Jul. 2002, No. 7, pp. 623-632, vol. 111.
Zoratto et al. "Hyolaryngeal Excursion as the Physiological Source of Swallowing Accelerometry Signals" Physiological Measurement, Jun. 2010, No. 6, pp. 843-855, vol. 31.
Smithard et al. "Complications and Outcome After Acute Stroke: Does Dysphagia Matter?" Stroke, Jul. 1996, No. 7, pp. 1200-1204, vol. 27.
Suiter et al. "Clinical Utility of the 3-Ounce Water Swallow Test" Dysphagia, Sep. 2008, No. 3, pp. 244-250, vol. 23.
Ramsey et al. "Silent Aspiration: What do we know?" Dysphagia, Sep. 2005, No. 3, pp. 218-225, vol. 20.
Daniels et al. "Clinical Assessment of Swallowing and Prediction of Dysphagia Severity" American Journal of Speech-Language Pathology, 1997, pp. 17-24, vol. 6.
Zoratto et al. "Hyolaryngeal Excursion as the Physiological Source of Swallowing Accelerometry Signals" Physiological Measurement, 2010, pp. 844-855, vol. 31.
Diagnosis and Treatment of Swallowing Disorders (Dysphagia) in Acute-Care Stroke Patients Agency for Healthcare Research and Quality, Mar. 1999.
Sejdic et al. "A Procedure for Denoising Dual-Axis Swallowing Accelerometry Signals" Physiological Measurement, Jan. 2010, No. 1, pp. N1-N9, vol. 31.
Sejdic et al. "Scaling Analysis of Baseline Dual-Axis Cervical Accelerometry Signals" Computer Methods and Programs in Biomedicine, Sep. 2011, No. 3, pp. 113-120, vol. 103.
Sejdic et al. "Segmentation of Dual-Axis Swallowing Accelerometry Signals in Healthy Subjects with Analysis of Anthropometric Effects on Duration of Swallowing Activities" IEEE Transactions on Biomedical Engineering, Apr. 2009, No. 4, pp. 1090-1097, vol. 56.
Sejdic et al. "Understanding the Statistical Persistence of Dual-Axis Swallowing Accelerometry Signals" Computers in Biology and Medicine, 2010, Nos. 11-12, pp. 839-844, vol. 40.

(56) References Cited

OTHER PUBLICATIONS

Sejdic et al. "Vocalization Removal for Improved Automatic Segmentation of Dual-Axis Swallowing Accelerometry Signals" Medical Engineering and Physics, Jul. 2010, No. 6, pp. 668-672, vol. 32.
Sejdic et al. "Baseline Characteristics of Dual-Axis Cervical Accelerometry Signals" Annals of Biomedical Engineering, Mar. 2010, No. 3, pp. 1048-1059, vol. 38.
Eisenstadt "Dysphagia and Aspiration Pneumonia in Older Adults" Journal of the American Academy of Nurse Practitioners, 2010, pp. 17-22, vol. 22.
Hanna et al. "Anthropometric and Demographic Correlates of Dual-Axis Swallowing Accelerometry Signal Characteristics: A Canonical Correlation Analysis" Dysphagia, Jun. 2010, No. 2, pp. 94-103, vol. 25.
Lotte et al. "A Review of Classification Algorithms for EEG-Based Brain-Computer Interfaces" Journal of Neural Engineering, 2007, R1-R3, vol. 4.
Bours et al. "Bedside Screening Tests vs. Videofluoroscopy or Fibreoptic Endoscopic Evaluation of Swallowing to Detect Dysphagia in Patients with Neurological Disorders: Systematic Review" Journal of Advanced Nursing, Mar. 2009, No. 3, pp. 477-493, vol. 65.
Orovic et al. "Time-Frequency Analysis and Hermite Projection Method Appied to Swallowing Accelerometry Signals" EURASIP Journal of Advances in Signal Processing, 2010, pp. 1-7, vol. 2010.
Jolliffe "Discarding Variables in a Principal Component Analysis. i: Artificial Data" Journal of the Royal Statistical Society, 1972, No. 1, pp. 21-31, vol. 22.
Logemann "Swallowing Disorders" Best Practice & Research Clinical Gastroenterology, 2007, No. 4, pp. 563-573, vol. 21.
Cichero et al. "Detection of Swallowing Sounds: Methodology Revisited" Dysphagia, 2002, No. 1, pp. 40-49, vol. 17.
Cichero et al. "Triaging Dysphagia: Nurse Screening for Dysphagia in an Acute Hospital" Journal of Clinical Nursing, Jun. 2009, No. 11, pp. 1649-1659, vol. 18.
Arvedson et al. "Silent Aspiration prominent in Children with Dysphagia" International Journal of Pediatric Otorhinolaryngology, Jan. 1994, pp. 173-181, vol. 28.
Rosenbek et al. "A Penetration-Aspiration Scale" Dysphagia, Mar. 1996, No. 2, pp. 93-93, vol. 11.
Hua et al. "Optimal Number of Features as a Functiono f Sample Size for Various Classification Rules" Bioinformatics, 2005, No. 8, pp. 1509-1515, vol. 21.
Coyle et al. "Oropharyngeal Dysphagia Assessment and Treatment Efficacy: Setting the Record Straight" Journal of the American Medical Directors Association, Jan. 2009, No. 1, pp. 62-66, vol. 10.
Lee et al. "Classification of Healthy and Abnormal Swallows Based on Accelerometry and Nasal Airflow Signals" Artificial Intelligence in Medicine, May 2011, No. 1, pp. 17-25, vol. 52.
Arvedson "Assessment of Pediatric Dysphagia and Feeding Disorders: Clinical and Instrumental Approaches" Developmental Disabilities Research Reviews, 2008, pp. 118-127, vol. 14.
Lee et al. "Swallow Segmentation with Artificial Neural Networks and Multi-Sensor Fusion" Medical Engineering and Physics, Nov. 2009, No. 9, pp. 1049-1055, vol. 31.
Lee et al. "Time and Time-Frequency Characterization of Dual-Axis Swallowing Accelerometry Signals" Physiological Measurement, Sep. 2008, No. 9, pp. 1105-1120, vol. 29.
Lee et al. "A Radial Basis Classifier for the Automatic Detection of Aspiration in Children with Dysphagia" Journal of NeuroEngineering and Rehab, 2006, pp. 1-17, vol. 3.
Youmans et al. "Normal Swallowing Acoustics Across Age, Gender, Bolus, Viscosity, and Bolus Volume" Dysphagia, 2011, pp. 374-384, vol. 26.
Hind et al. "Comparison of Train Clinician Ratings with Expert Ratings of Aspiration on Videofluoroscopic Images from a Random Clinical Trial" Dysphagia, 2009, pp. 211-217, vol. 24.
Logemann "The Evaluation and Treatment of Swallowing Disorders" Current Opinion in Otolaryngology & Head and Neck Surgery 1998, pp. 395-400, vol. 6.

Prasse et al. "An Overview of Pediatric Dysphagia" Clinical Pediatrics, 2009, pp. 247-251, vol. 48.
Takahashi et al. "Methodology for Detecting Swallowing Sounds" Dysphagia, Dec. 1994, No. 1, pp. 54-62, vol. 9.
Bryant et al. "VFS Interjudge Reliability Using a Free and Directed Search" Dysphagia, 2011, pp. 1-11.
Perry "Screening Swallowing Function of Patients with Acute Stroke. Part Two" Journal of Clinical Nursing, Jul. 2001, No. 4, pp. 474-481, vol. 10.
Pikus et al. "Videofluoroscopic Studies of Swallowing Dysfunction and the Relative Risk of Pneumonia" Am Journal of Roentgenology, Jun. 2003, No. 6, pp. 1613-1616, vol. 180.
Greco et al. "Instrumentation for Bedside Analysis of Swallowing Disorders" 32nd Annual Intl Conf of IEEE, Sep. 2010.
Lof et al. "Test-Retest Variability in Normal Swallowing" Dysphagia, 1990, pp. 236-242, vol. 4.
Lefton-Greif et al. "Pediatric Feeding and Swallowing Disorders" Seminars in Speech and Language, Aug. 2007, No. 3, pp. 161-165, vol. 28.
Lefton-Greif et al. "Pediatric Dysphagia" Physical Medicine and Rehabilitation Clinics of North America, Nov. 2008, No. 4, pp. 837-851, vol. 19.
Rugiu "Role of Videofluoroscopy in Evaluation of Neurologic Dysphagia" Acta Otorhinolaryngologica Italica, Dec. 2007, No. 6, pp. 306-316, vol. 27.
Trapl et al. "Dysphagia Bedside Screening for Acute-Stroke Patients" Stroke, Nov. 2007, No. 11, pp. 2948-2952, vol. 38.
"Management of Patients with Stroke: Identification and Management of Dysphagia" Scottish Intercollegiate Guidelines Network, Edinburgh, Scotland, Jun. 2010.
Reddy et al. "Measurements of Acceleration during Videofluorographic Evaluation of Dysphagic Patients" Medical Engineering & Physics, Jul. 2000, No. 6, pp. 405-412, vol. 22.
Reddy et al. "Noninvasive Acceleration Measurements to Characterize the Pharyngeal Phase of Swallowing" Journal Biomedical Engin, Sep. 1991, No. 5, pp. 379-383, vol. 13.
Paik et al. "Movement of the hyoid bone and the epiglottis during swallowing . . . " Journal of Electromyography and Kinesiology, Apr. 2008, No. 2, pp. 329-335, vol. 18.
Reddy et al. "Toward classification of dysphagic patients using biomechanical measurements" Journal of Rehabilitation Research & Development, 1994, No. 4, pp. 335-344, vol. 31.
Clave et al. "Accuracy of the volume-viscosity swallow test for clinical screening of oropharyngeal dysphagia . . . " Clinical Nutrition, Dec. 2008, No. 6, pp. 806-815, vol. 27.
Lisboa et al. "The use of artificial neural networks in decision support in cancer: A systematic review" Neural Networks, May 2006, No. 4, pp. 408-415, vol. 19.
Leslie et al. "Reliability and validity of cervical auscultation: A controlled comparison using videofluoroscopy" Dysphagia, Sep. 2004, No. 4, pp. 231-240, vol. 19.
Lindsay et al. "Canadian best practice recommendations for stroke care" Canadian Medical Association Journal, Dec. 2008, No. 12, pp. E1-E93, vol. 179.
Martino et al. "A Sensitivity Analysis to Determine whether Ten Teaspoons of Water are really Necessary" Dysphagia, Dec. 2009, No. 4, p. 473, vol. 24.
Martino et al. "The Toronto Bedside Swallowing Screening Test: Development and Validation of Dysphagia Screening Tool for Patients with Stroke" Stroke, Feb. 2009, No. 2. pp. 555-561.
Martino et al. "Dysphagia after Stroke: Incidence, Diagnosis, and Pulmonary Complications" Stroke, Dec. 2005, No. 12, pp. 2756-2763, vol. 36.
Esteves et al. "Configurable Portable/Ambulatory Instrument for the Analysis of the Coordination Between Respiration & Swallowing" 32nd Annual Intl Conf of IEEE, Sep. 2010.
Tawfik et al. "Caregivers' Perceptions Following Gastrostomy in Severely Disabled Children with Feeding Problems" Develop Medicine Child Neurology, Nov. 1997, No. 11, pp. 74.
Leder et al. "Fiberoptic Endoscopic Evaluation of Dysphagia to Identify Silent Aspiration" Dysphagia, Jan. 1998, No. 1, pp. 19-21, vol. 13.

(56) References Cited

OTHER PUBLICATIONS

Leder et al. "Silent Aspiration Risk is Volume-Dependent" Dysphagia, Sep. 2011, No. 3, pp. 304-309, vol. 26.

Damouras et al. "An Online Swallow Detection Algorithm . . . Dual-Axis Accelerometry" IEEE Transactions on Signal Processing, Jun. 2010, No. 6, pp. 3352-3359, vol. 58.

Sejdic et al. "The Effects of Head Movement on Dual-Axis Cervical Accelerometry Signals" BMC Research Notes, 2010, vol. 3.

Daniels et al. "Aspiration in Patients with Acute Stroke" Archives of Physical Medicine and Rehabilitation, Jan. 1998, No. 1, pp. 14-19, vol. 79.

Hamlet et al. "Interpreting the Sounds of Swallowing: Fluid Flow Through the Cricopharynegeus" The Annals of Otology, Rhinology, & Laryngology, 1990, No. 9, pp. 749-752, vol. 99.

Moriniere et al. "Origin of the Sound Components during Pharyngeal Swallowing in Normal Subjects" Dysphagia, Sep. 2008, No. 3, pp. 267-273, vol. 23.

Raudys et al. "Small Sample Size Effects in Statistical Pattern Recognition: Recommendations for Practitioners" IEEE Transactions on Pattern Analysis, 1991, pp. 525-564.

Singapore Ministry of Health "Stroke & Transient Ischaemic Attacks: Assessment, Investigation, Immediate Management & Secondary Prevention" Clinical Practice Guidelines, 2009.

Smithard et al. "Can Bedside Assessment Reliably Exclude Aspiration Following Acute Stroke?" Age & Ageing, 1998, pp. 99-106, vol. 27.

Chau "A Review of Analytical Techniques for Gait Data. Part 2: Neural Network and Wavelet Methods" Gait and Posture, Apr. 2001, No. 2, pp. 102-120, vol. 13.

Chau et al. "Investigating the Stationarity of Paediatric Aspiration Signals" Transactions on Neural Systems and Rehabilitation Engineering, Mar. 2005, No. 1, pp. 99-105, vol. 13.

Rutala et al. "Guideline for Disinfection and Sterilization in Healthcare Facilities" Centers for Disease Control and Prevention, Atlanta, GA, 2008.

Dodds et al. "Influence of Bolus Volume on Swallow-Induced Hyoid Movement in Normal Subjects" Am. Journal of Roentgenology, Jun. 1988, No. 6, pp. 1307-1309, vol. 150.

Kim et al. "Maximum Hyoid Displacement in Normal Swallowing" Dysphagia, Sep. 2008, No. 3, pp. 274-279, vol. 23.

Youmans et al. "An Acoustic Profile of Normal Swallowing" Dysphagia, 2005, pp. 195-209, vol. 20.

Japan Office Action for Application No. P2013-548708, Dispatch No. 561524, dated Dec. 8, 2015, 4 pages.

* cited by examiner

| Parameter of Interest | Level of Comparison | Sensitivity | Specificity | Negative Predictive Value | Positive Predictive Value | Relative Risk |
|---|---|---|---|---|---|---|
| Impaired Swallowing Safety | Bolus (sip or mouthful) | 90% | 77% | 97% | 49% | 3.99 |
| | Sub-swallow | 85% | 77% | 92% | 62% | 3.70 |
| | Participant (aggregate across all observed swallows) | 100% | 54% | 100% | 54% | 2.17 |
| Dysphagia (either impaired swallowing safety and/or impaired efficiency) | Bolus (sip or mouthful) | 81% | 76% | 49% | 94% | 3.37 |
| | Sub-swallow | 44% | 60% | 29% | 74% | 1.10 |
| | Participant (aggregate across all observed swallows) | 62% | 100% | 6% | 100% | n/a (no false positives) |

FIGURE 7

| PARAMETER | STATISTIC | PER SWALLOW | PER PARTICIPANT |
|---|---|---|---|
| ASPIRATION RISK (N = 13 PATIENTS; 80 SWALLOWS) | SENSITIVITY (Sn) | 85% | 100% |
| | SPECIFICITY (Sp) | 77% | 54% |
| | ACCURACY (MEAN OF Sn + Sp) | 81% | 77% |
| | FALSE NEGATIVE RATE | 8% | 0% |
| | FALSE POSITIVE RATE | 38% | 48% |
| | NEGATIVE PREDICTIVE VALUE | 92% | 100% |
| | POSITIVE PREDICTIVE VALUE | 62% | 54% |
| | RELATIVE RISK | 3.70 | 2.17 |

FIGURE 8

METHOD AND DEVICE FOR SWALLOWING IMPAIRMENT DETECTION

CROSS REFERENCE TO RELATED APPLICATIONS

The present application is a National Stage of International Application No. PCT/CA2012/000036, filed on Jan. 18, 2012, which claims priority to U.S. Provisional Patent Application No. 61/433,750, filed Jan. 18, 2011, the entire contents of which are being incorporated herein by reference.

FIELD OF THE DISCLOSURE

The present disclosure relates to swallowing impairments, and in particular, to a method and device for swallowing impairment detection.

BACKGROUND

Dysphagia is a serious component of many neurological diseases and injuries. The incidence of dysphagia following stroke has been reported to be 37-78% across studies, with aspiration incidence estimated at 43-54% in those with dysphagia. One systematic review has concluded that stroke patients who aspirate face 11.56 times the risk of developing pneumonia, compared to those without dysphagia. Patients who are aspirate, have been shown to be 10 times more likely ($p<0.0001$) to develop pneumonia in the ensuing 6 months than those with normal swallowing. These figures speak to the importance of identifying dysphagia and managing aspiration risk as early as possible, both in potentially avoiding numerous aspiration-related deaths, and in saving the healthcare system considerable amounts of money by providing early treatment. Over the past decade, numerous evidence-based best practice guidelines have arrived at similar conclusions, strongly endorsing the early implementation of screening protocols to identify dysphagia and aspiration in high-risk populations, such as those with stroke.

Aspiration, generally understood as the entry of foreign contents into the upper airway, is a serious concern for individuals with swallowing difficulty (dysphagia), and can lead to pneumonia, for example. For instance, prandial aspiration, or the entry of foreign material into the upper airway during swallowing, is a serious component of dysphagia.

Using known and particularly invasive techniques, such as videofluoroscopic swallowing examinations, aspiration severity may be sub-classified based on the observed depth of airway invasion. For example, transient entry of material into the laryngeal vestibule, above the vocal cords, is termed high penetration (or a score of 2 on the 8-point Penetration Aspiration Scale); scores of 3-5, termed penetration, apply when material enters the laryngeal vestibule without subsequent clearance, and aspiration is the term used when material crosses the vocal cords and enters the trachea (scores of 6-8). A major dilemma for the detection of aspiration is the fact that overt clinical signs (e.g., cough or throat clearing) are reportedly absent up to 67% of the time; this is called "silent aspiration". The risk of developing pneumonia has been found to be 4, 10, and 13 times greater, respectively, in patients with penetration, aspiration, or silent aspiration on videofluoroscopy, compared to individuals with normal swallowing. Evidence-based best practice guidelines concur that screening protocols should be used to facilitate the prompt identification and management of aspiration risk in high-risk populations, such as stroke patients; however, currently implemented protocols to this end often fail to provide satisfactory results, or again, achieve reasonable results at the expense of requiring the application of relatively invasive procedures.

In addition to aspiration, swallowing inefficiency is a major concern in individuals with dysphagia. Swallowing inefficiency is defined as the inability to swallow the contents of a single bolus (or mouthful) in a maximum of 2 swallows. This frequently leads to the presence of residual material being left behind in the throat (pharynx) after the swallow. The presence of this leftover material is, in turn, a risk for aspiration.

The main goals of a swallow screening protocol are generally two-fold: 1) to identify risk of impaired swallowing safety, i.e. penetration (entry of material into the airway above the level of the vocal cords) and/or aspiration (entry of material into the airway below the level of the vocal cords); and 2) to identify risk of impaired swallowing efficiency, characterized either by the presence of residues in the pharynx after the swallow, and/or prolonged transit times for moving a bolus in entirety from the mouth into the esophagus. To date, the principal emphasis in health policy calls for swallow screening has been on the first of these goals, that is the identification of penetration and/or aspiration risk (henceforth, "P-A risk"). When patients are identified to have either dysphagia or P-A risk through screening, they are generally referred for comprehensive swallowing assessment.

Unfortunately, the clinical identification of impaired swallowing safety and efficiency related to dysphagia is not particularly straightforward. Under usual circumstances, healthy awake people will swallow reflexively when material penetrates the airway above the vocal cords, and will cough when this material is aspirated below the vocal cords. Current P-A risk screening tools rely heavily on the recognition of overt clinical signs that imply possible aspiration: coughing, throat clearing, changes in respiratory rate, and changes in voice quality. In those with neurologic injury, however, overt clinical signs are frequently absent or volume-dependent. As noted above, silent aspiration is reported to occur in 25%-67% of acute stroke patients, and in 28% of patients overall, according to some studies. The variable expression of overt clinical signs of impaired swallowing safety in patients with neurogenic dysphagia contributes to limited success in P-A risk detection through clinical screening, and means that screeners must be trained to be alert for signs that are subtle. Similarly, post-swallow residues, related to swallowing inefficiency, are not reliably detectable at the bedside based on the observation of clinical signs, or based on asking patients whether they feel material sticking in their throats.

For example, current clinical approaches to non-invasive screening for aspiration typically involve the swallowing of water. The clinician notes signs of difficulty, including cough, post-swallow throat clearing, or voice changes that might imply the presence of liquid around the vocal cords. However, studies differ in their conclusions regarding the validity of abnormal clinical signs for revealing aspiration, compared to blinded ratings of instrumental assessments, and screening protocols involving sips of water tend to over-identify aspiration risk with false-positive rates as high as 72%.

Furthermore, current approaches to screening frequently rely on nurses to administer/conduct screening protocols. One widely-promoted clinical screening protocol (the Tor- BSST) has an accompanying training package, which involves initial training of 8 hours for a lead clinician/champion/trainer who then delivers training of 4 hours for individuals who will administer the screening protocol. However, institutional barriers have been reported to prevent implementation of screening guidelines, even after such extensive training. Given the turnover of nursing staff, a strong institutional commitment to continuing skills training and credentialing is required on a long-term basis.

Given the variable performance of swallow screenings for detecting aspiration, and the burden that this approach involves for training and competency-maintenance, a need exists for a valid non-invasive instrumental method to reliably detect impaired swallowing safety and efficiency, for example in a clinical setting or at the bedside. While the appraisal of swallowing sounds or vibrations has been proposed as a candidate method, available studies have heretofore been unsuccessful at attaining valid identification of aspiration. Accordingly, valid, reliable tools for detecting aspiration and other related swallowing impairments are needed that overcome the variable predictive utility of known clinical screening protocols and/or reduce the substantial burden on nursing staff imposed by the implementation of such protocols.

Therefore, there remains a need for a method and device for swallowing impairment detection that overcomes some of the drawbacks of known techniques, or at least, provides a useful alternative.

This background information is provided to reveal information believed by the applicant to be of possible relevance to the invention. No admission is necessarily intended, nor should be construed, that any of the preceding information constitutes prior art against the invention.

SUMMARY

An object of the invention is to provide a method and device for swallowing impairment detection. In accordance with one embodiment, there is provided a device for use in identifying a possible swallowing impairment in a candidate during execution of a swallowing event, the device comprising: a dual axis accelerometer to be positioned in a region of the candidate's throat and configured to acquire axis-specific vibrational data representative of the swallowing event; a processing module operatively coupled to said accelerometer for processing said axis-specific data to extract therefrom, for each axis, one or more features representative of the swallowing event, and classify said vibrational data as indicative of one of normal swallowing and possibly impaired swallowing based on said extracted features.

In accordance with another embodiment of the invention, there is provided a method for classifying cervical dual-axis accelerometry data acquired in respect of a candidate swallowing event to identify a possible swallowing impairment, comprising: receiving as input axis-specific vibrational data representative of the swallowing event; extracting one or more preset features representative of the swallowing event for each axis of said axis-specific vibrational data; comparing said extracted features with preset classification criteria defined as a function of said preset features; and outputting, based on said comparing step, classification of said vibrational data as indicative of one of normal swallowing and possibly impaired swallowing.

In accordance with another embodiment of the invention, there is provided a computer readable-medium having statements and instructions stored thereon for implementation by a processor to automatically implement the above method.

In accordance with another embodiment of the invention, there is provided a method for identifying a possible swallowing impairment in a candidate via execution of one or more preset swallowing events, comprising: recording dual-axis vibrational data representative of said one or more swallowing events; extracting one or more swallowing-event specific features for each axis of said dual-axis vibrational data; and classifying said extracted features as indicative of one of normal swallowing and possibly impaired swallowing.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 7 is a table of performance results (detection of impaired swallowing safety and the combination of impaired swallowing safety with impaired swallowing efficiency) achieved in accordance with one embodiment of the invention;

FIG. 8 is a table of further aspiration-detection performance results, in accordance with the embodiment of FIG. 7.

DETAILED DESCRIPTION

Figure 1:
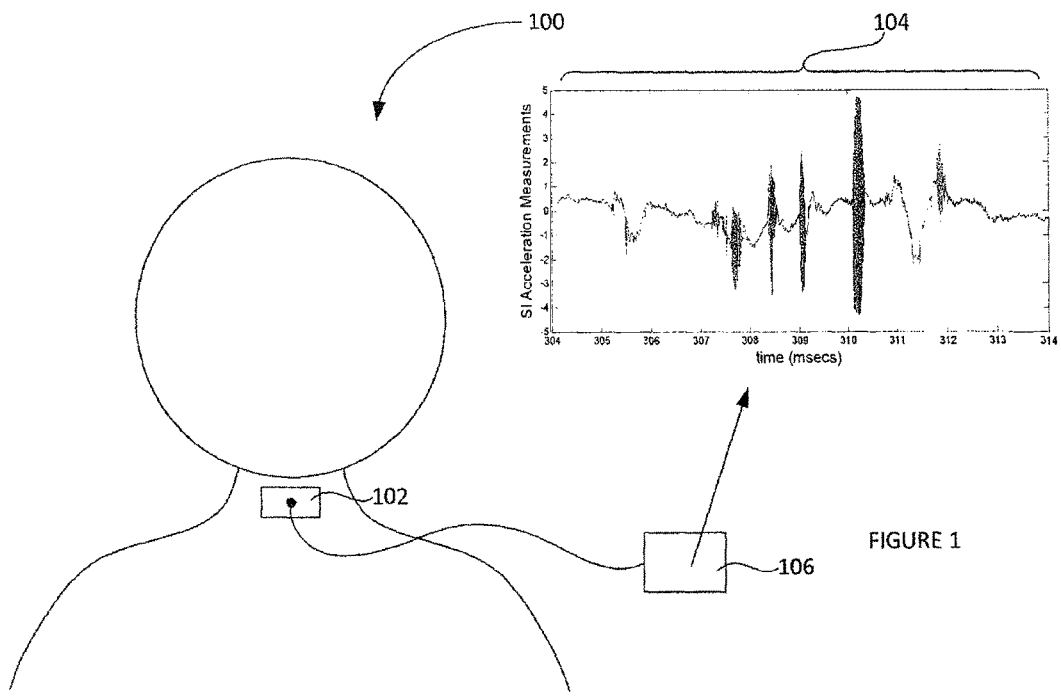
FIG. 1 is a schematic diagram of a swallowing impairment screening device in operation, in accordance with one embodiment of the invention.

As introduced above, aspiration, generally understood as the entry of foreign contents into the upper airway, is a serious concern for individuals with swallowing difficulty, for example suffering from dysphagia or other such conditions, and can lead to pneumonia, for example. Unfortunately, aspiration is not always readily identified, due to the variable expression of overt clinical signs, such as cough. Other swallowing impairments, such as the presence of residues post-swallowing, which is common in patients suffering from dysphagia, are also of concern, and the detection thereof is generally required in properly screening for and/or diagnosing a patient's condition. The herein described swallowing impairment detection methods and devices provide a solution to the widespread need for an accurate, non-invasive instrument to detect impaired swallowing safety and/or efficiency during screening. As will be elaborated below, such methods and devices now provide for the greater ability to incorporate swallowing impairment screening into routine nursing assessments of patient vital signs, in some embodiments, with minimal training.

For instance, the methods and devices described herein provide various improvements over the state of the art that assist in the screening for, detection of, monitoring and/or diagnostic of swallowing impairment(s). It will be appreciated that while specific embodiments are described herein in the context of specific applications and implementations, the various features of the herein described methods, devices, and elements thereof, may be considered in different contexts to improve different aspects associated with swallowing impairment screening, detection, monitoring and/or diagnostics, and that, with different levels of user interaction, automation and complexity depending on the application at hand. Namely, while certain implementation protocols and operation guidelines may be considered herein with respect to specific examples, alternative or complimentary approaches may also be considered without departing from the general scope and nature of the present disclosure. Accordingly, it will be appreciated that the use herein of the term "impairment detection" is meant be construed broadly to encompass different levels of impairment identification, be it in the context of routine screenings or diagnostics, and that, without departing from the general scope and nature of the present disclosure.

As will be discussed in greater detail below, the methods and devices described herein make use of dual-axis cervical accelerometry for detecting swallowing impairment(s), for example, in individuals with suspected dysphagia. In one example, screening for potential aspiration events in different subjects is implemented via analysis of cervical vibrations during thin liquid swallows, or in executing other types of swallowing events as necessary or appropriate given a specific screening or diagnostic protocol, device programming or configuration, and other such considerations. Features extracted from acquired dual-axis accelerometry signals, can be effectively and automatically classified to allow a user or operator of the disclosed device/aspirometer to identify individual swallowing events as one of a normal event or as one representative of a possible aspiration event. Upon applying certain screening/diagnostic protocols and/or guidelines, candidates at risk of aspiration may thus be identified as such using the disclosed methods and devices considered herein, wherein such identification may lead to further assessment, diagnostics, treatment and/or dietary restrictions, as deemed appropriate.

Similarly, screening for other swallowing impairments, such as swallowing efficiency impairments generally manifested by the presence of residues post-swallow, can also or alternatively be detected by the herein described embodiments of the invention. As will be appreciated by the skilled artisan, where the below description refers more specifically to an aspiration detection method or device (e.g. swallowing safety impairment detection/screening), a similar implementation may be considered for the detection or screening of other swallowing impairments, such as swallowing efficiency impairments, and that, without departing from the general scope and nature of the present disclosure.

For example, in some embodiments, the swallowing impairment detection device can be configured to provide indication of both impaired swallowing safety and impaired swallowing efficiency during swallow screening. Namely, swallowing vibration signals recorded on the neck are understood to be generated primarily as the result of structural movement of the hyoid and larynx, but these signals have also been demonstrated to carry information related to swallowing safety and efficiency. Through filtering and processing of signals collected with a dual-axis accelerometer placed just below the thyroid cartilage, one or more classifiers, as disclosed herein, can be trained to discriminate between signals associated with penetration-aspiration and those displaying normal swallowing safety, and/or trained to discriminate between signals associated with reduced swallowing efficiencies and those displaying normal swallowing efficiencies.

As will be described in the below Example, in a study of 40 individuals undergoing concurrent videofluoroscopy, an aspirometer, configured in accordance with one embodiment of the invention, was able to identify impaired swallowing safety, at the level of a single 5 cc thin liquid bolus, with 90% sensitivity and 77% specificity. In another example, screening for a broader construct of "dysphagia" was implemented, whereby the device was adapted to not only identify candidates manifesting unsafe swallows (e.g. classifying one or more swallowing events as healthy or as a potential aspiration event) but also to identify swallowing inefficiencies, that is, the manifestation of post-swallow residues. This further classification of a candidate's condition (i.e. either impaired safety and/or impaired efficiency) was identified with 81% sensitivity and 76% specificity using this particular embodiment of the device.

To achieve these results, the classifier(s), as described in greater detail below, was trained against known results achieved via concurrent VFSS, and results of such training used to comparatively classify corresponding dual-axis accelerometric signals with a high level of success, as reported above. Accordingly, the classifier(s) described below was demonstrated to provide a useful tool in the screening for both swallowing safety and efficiency, which potential has heretofore only been available via invasive VFSS.

In one particular example, accelerometry signals associated with three teaspoon-sized thin liquid swallows and a cup-drinking task were collected. Collected signals were processed to remove artifacts, in one example, and then processed via a trained classifier module to identify signals suspected to contain penetration (entry of material into the laryngeal vestibule above the level of the vocal cords) or aspiration. The validity of this approach was measured versus blinded ratings of penetration-aspiration obtained via concurrent videofluoroscopy. Utility statistics computed in respect of the applied accelerometry classifier for detecting penetration-aspiration showed, on a bolus-by-bolus basis, 90% sensitivity and 77% specificity. Given that a single sip or mouthful (i.e., a "bolus") may lead to more than one swallow, when the swallows associated with each bolus were further subdivided into subswallows, the accuracy of detecting penetration-aspiration per swallow was 85% sensitivity and 77%. When all swallowing tasks were considered in aggregate, i.e. on a participant-by-participant basis, the classifier achieved 100% sensitivity and 54% specificity. Accordingly, as will be discussed in greater detail below, it was concluded that dual-axis accelerometry, as implemented within the context of the different embodiments of the invention described herein, shows a strong performance for accurately detecting airway invasion in thin liquid swallowing, both at the level of the single swallow and across a sequence of swallows, thus allowing dual axis accelerometry, as discussed herein, to be used to support valid, reliable and efficient detection of aspiration risk in patients with suspected dysphagia, or other such conditions. It will be appreciated that while studies conducted for this purpose, and discussed within the context of the following disclosure, were focused on patients with suspected dysphagia, similar approaches may be considered within the context of the present disclosure to apply to patients at risk for or manifesting symptoms of other related conditions.

With reference to FIG. 1, a system for use in swallowing impairment detection, generally referred to using the numeral 100, and in accordance with an illustrative embodiment of the invention, will now be described. In this example, the system 100 generally comprises a dual axis accelerometer 102 to be attached in a throat area of a candidate for acquiring dual axis accelerometry data and/or signals during swallowing (e.g. see illustrative S-I Acceleration signal 104 shown in FIG. 1). For example, accelerometry data may include, but is not limited to, throat vibration signals acquired along the anterior-posterior axis (A-P) and superior-inferior axis (S-I).

In one embodiment, the accelerometer is also fitted with a pressure sensor or pressure sensitive film configured to effectively measure a pressure between the accelerometer and the candidate's throat when installed (e.g. measure a pressure applied by the accelerometer on the candidate's throat as a function of a tension in a strap or elasticized band used to secure the accelerometer in position). Therefore, upon monitoring this pressure, for example via an indicator on a user interface associated with the device, a clinician may be better able to position the accelerometer on each candidate with reproducible accuracy, thus reducing the likelihood of improper positioning/installation and thus, reducing data errors or improving overall performance accuracy of the device. In other embodiments, the accelerometer may rather be positioned via the application of dual-sided adhesive tape, or the like.

In some embodiments, signal quality and/or accelerometer positioning/placement may be otherwise tested and/or monitored via a testing protocol, whereby an acquired test signal, for example, may be checked for consistency with system calibration and/or preset normal operating conditions. For example, a test signal may be acquired during a non-swallowing task, such as the candidate turning its head or saying 'ah', and such test signal compared with one or more preset test signal ranges and/or characteristics. This and other similar testing procedures can be applied before, during and/or after different segments of the swallowing impairment detection protocol, as will be appreciated by the skilled artisan, without departing from the general scope and nature of the present disclosure.

The accelerometer is operatively coupled to a swallowing data processing module or aspirometer 106 configured to process the acquired data for swallowing impairment detection. Note that the term "aspirometer" is used generically herein to refer not only to a device for aspiration detection, but also to similar devices also configured for the detection of other swallowing impairments, such as swallowing inefficiencies. The processing module 106 is depicted herein as a distinctly implemented device, or aspirometer, operatively coupled to accelerometer 102 for communication of data thereto, for example, via one or more data communication media such as wires, cables, optical fibres, and the like, and/or one or more wireless data transfer protocols, as would be readily appreciated by one of ordinary skill in the art. The processing module may, however, in accordance with another embodiment, be implemented integrally with the accelerometer, for example, depending on the intended practicality of the aspirometer, and/or context within which it is to be implemented. As will be appreciated by the skilled artisan, the processing module may further be coupled to, or operated in conjunction with, an external processing and/or interfacing device, such as a local or remote computing device or platform provided for the further processing and/or display of raw and/or processed data, or again for the interactive display of system implementation data, protocols and/or screening/diagnostics tools.

Figure 2:
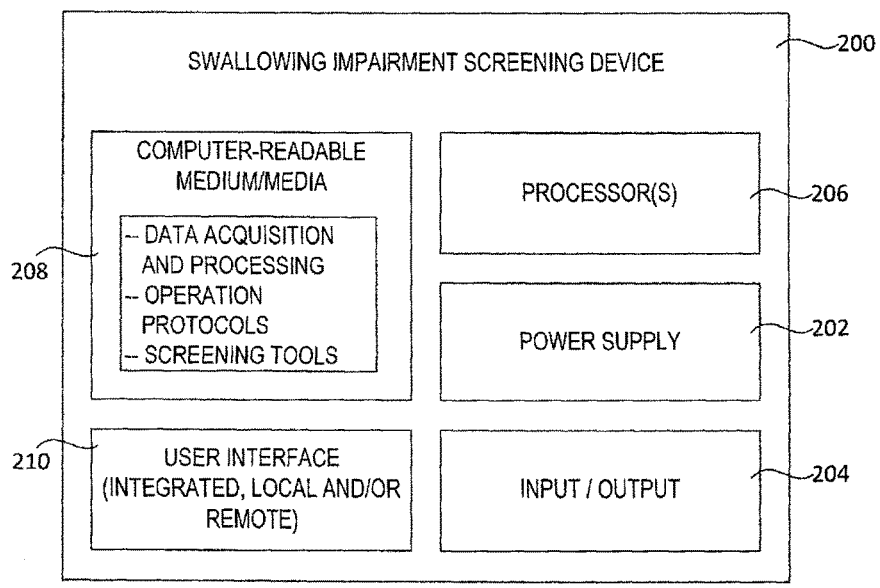
FIG. 2 is a schematic diagram of a swallowing impairment detection device, and components thereof, in accordance with one embodiment of the invention.

With reference to FIG. 2, the processing module, depicted herein generically as a self-contained device or aspirometer 200, generally comprises a power supply 202, such as a battery or other know power source, and various input/output port(s) 204 for the transfer of data, commands, instructions and the like with interactive and/or peripheral devices and/or components (not shown), such as for example, a distinctly operated accelerometer (as shown in FIG. 1), external data processing module, display or the like. The device 200 further comprises one or more computer-readable media 208 having stored thereon statements and instructions, for implementation by one or more processors 206, in automatically implementing various computational tasks with respect to, for example, accelerometer data acquisition and processing, operation of the device in accordance with a given or selected impairment detection protocol (e.g. one or more clinically accepted operation protocols, testing and/or validation sequences, etc.), or again in the implementation of one or more impairment detection, monitoring, screening and/or diagnostic tools implemented on or in conjunction with the device 200. The device 200 may further comprise a user interface 210, either integral thereto, or distinctly and/or remotely operated therefrom for the input of data and/or commands (e.g. keyboard, mouse, scroll pad, touch screen, push-buttons, switches, etc.) by an operator thereof, and/or for the presentation of raw, processed and/or screening/diagnostic data with respect to swallowing impairment detection, monitoring, screening and/or diagnostic (e.g. graphical user interface such as CRT, LCD, LED screen, touchscreen, or the like, visual and/or audible signals/alerts/warnings/cues, numerical displays, etc.)

As will be appreciated by those of ordinary skill in the art, additional and/or alternative components operable in conjunction and/or in parallel with the above-described illustrative embodiment of device 200 may be considered herein without departing from the general scope and nature of the present disclosure. It will further be appreciated that device 200 may equally be implemented as a distinct and dedicated device, such as a dedicated home, clinical or bedside impairment detection device, or again implemented by a multi-purpose device, such as a multi-purpose clinical or bedside device, or again as an application operating on a conventional computing device, such as a laptop or PC, or other personal computing devices such as a PDA, smartphone, tablet or the like.

Figure 3:
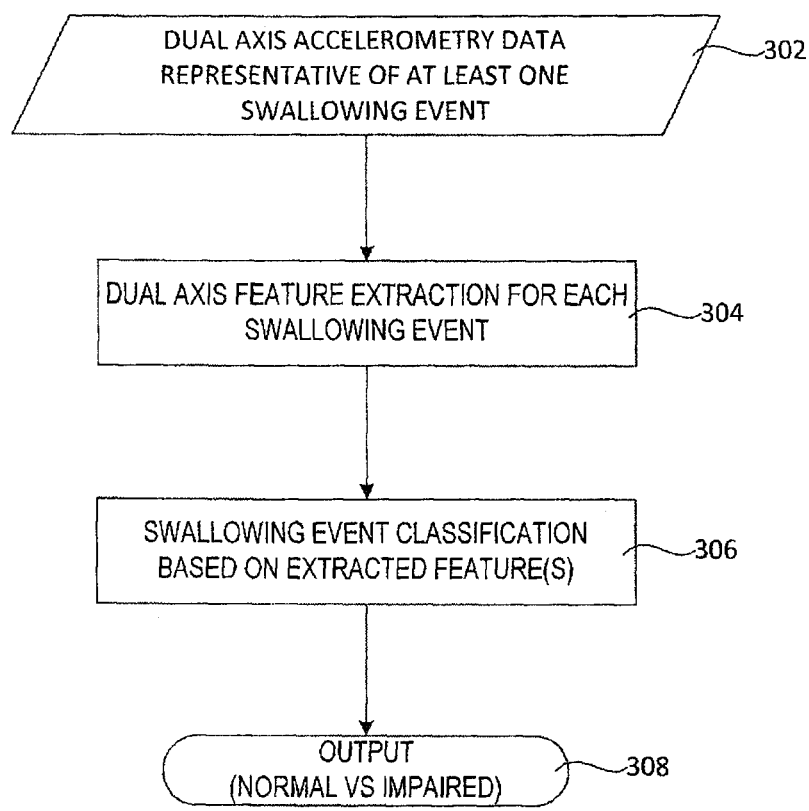
FIG. 3 is a high level dual axis accelerometry data processing flow diagram for implementation by a swallowing impairment detection device, in accordance with one embodiment of the invention.

With reference to FIG. 3, an example of a data processing stream, in accordance with one embodiment of the invention, will now be described. In general terms, the processing of acquired or collected dual axis accelerometry data 302 representative of at least one swallowing event may be composed of two broad steps, namely a dual axis feature extraction step 304 applied for data representative of each swallowing event along each axis, and a swallowing event classification step 306 based on the extracted feature(s) of step 304. In applying this approach to dual axis cervical accelerometry data representative of respective swallowing events, such swallowing events may be effectively classified as one of normal swallowing events and potentially impaired swallowing events (e.g. unsafe and/or inefficient), which classification output 308 may then be utilized in screening/diagnosing the tested candidate in question and allocating thereto appropriate treatment, further testing, and/or proposing various dietary or other related restrictions thereto until further assessment and/or treatment may be applied.

As will be appreciated by the person of ordinary skill in the art upon reference to the following description of specific examples, wherein greater detail is provided in qualifying different possibilities for the implementation of these steps in accordance with different embodiments of the invention, the nature of these steps substantially remains the same in achieving swallowing event classification. As will be further appreciated by the skilled artisan, while the above and following refer to data processing steps, it will be appreciated that such processes may be implemented, in accordance with different embodiments of the invention, by various processing techniques and approaches, which may for example, be subdivided into distinct, cooperative and/or interactive processing subroutines, modules or the like, and that, without departing from the general scope and nature of the present disclosure. For clarity, the processing steps have and will be described below as distinct processing steps or modules, however, it will be appreciated that a swallowing impairment detection device or computer-readable medium embodied therein comprising statements and instructions for implementation by a processor thereof in accomplishing a swallowing impairment detection method, in accordance with different embodiments of the invention, may be characterized by cooperative, parallel, successive and/or distinct processing modules that, in combination, achieve the results considered herein, without departing from the general scope and nature of the present disclosure.

Figure 4:
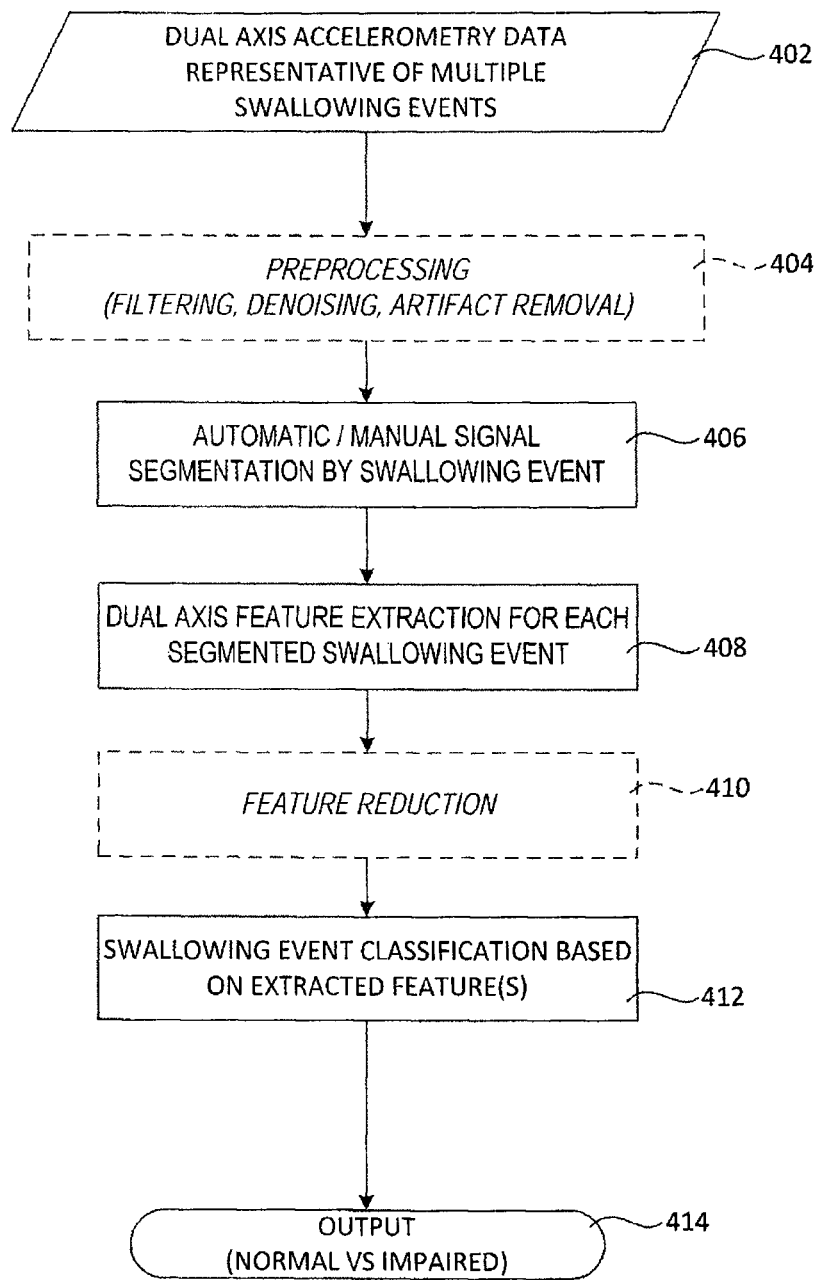
FIG. 4 is an illustrative dual axis accelerometry data processing flow diagram, showing optional steps in dashed-line boxes, for implementation by a swallowing impairment detection device, in accordance with one embodiment of the invention.

With reference to FIG. 4, and in accordance with an embodiment of the invention, a further illustrative dual axis accelerometry data processing flow will be described, wherein optional steps in this embodiment are shown in dashed-line boxes. In this particular embodiment, accelerometry data 402 is acquired or provided in respect of multiple swallowing events. This data is then processed via an optional preprocessing module 404 configured to condition the raw data and thus facilitate further processing thereof. For example, the raw data may be filtered, denoised and/or processed for signal artifact removal.

The preprocessed data is then automatically or manually segmented into distinct swallowing events (step 406). For example, an automated swallowing event segmentation process, such as described in co-pending United States Patent Application Publication No. 2010/0160833, the entire contents of which are incorporated herein by reference, may be applied to the data to segment this data by swallowing event. Alternatively, manual segmentation may be applied, for example, upon visual inspection of the data (e.g. identification of the start of each swallowing event, which may be readily and systematically recognized by an operator of the device). Alternatively, the device and method, in accordance with one embodiment, may involve segmented data recordal, as will be described further with reference to the exemplary protocol depicted in FIG. 6, whereby data is explicitly recorded for each swallowing event individually. In such embodiments, it will be appreciated that swallowing event-specific data may be preprocessed individually, thus effectively applying the manual signal segmentation step 406 of FIG. 4 during acquisition of accelerometry data 402 and prior to preprocessing step 404. As will be appreciated by the skilled artisan, these and other such variations may be considered herein without departing from the general scope and nature of the present disclosure.

The event-specific data is then processed by a dual axis feature extraction module 408, and optionally, a feature reduction module 410, allowing for each swallowing event to be classified at step 412 based on these extracted features. As discussed above generally, such classification thus allows for the determination and output 414 of which swallowing event represented a normal swallowing event as compared to a potentially unsafe and/or inefficient swallowing event.

Figure 5A:
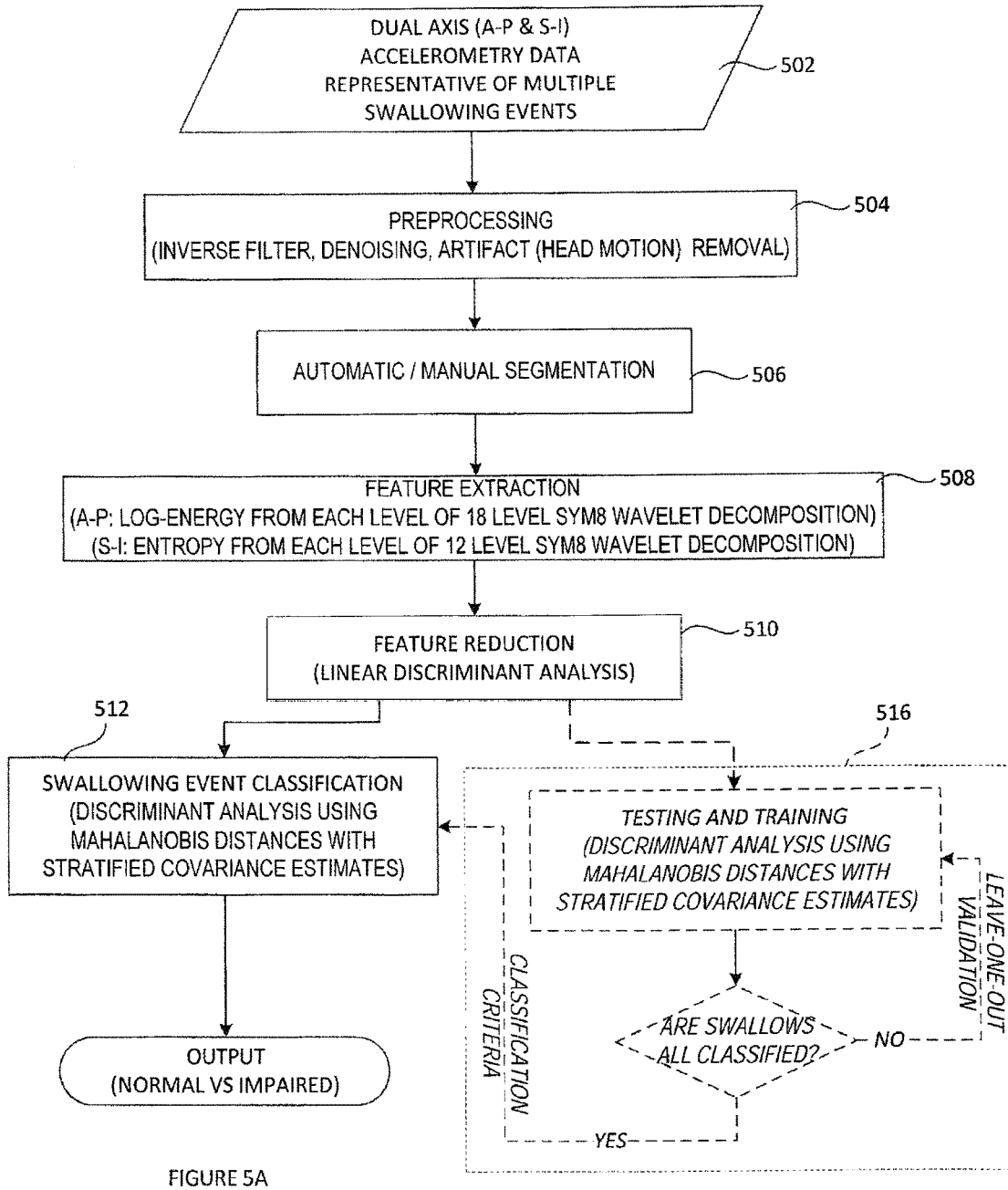
FIG. 5A is a detailed dual axis accelerometry data processing flow diagram for implementation by a swallowing impairment detection device, in accordance with one embodiment of the invention.

With reference to FIG. 5A, a detailed dual axis accelerometry data processing stream will be described, showing therein specific examples of processing techniques applicable with respect to some of the general processing modules described above at a higher level. It will be appreciated that while the following provides specific examples, such examples are not intended to limit the general scope of the present disclosure, but are rather presented solely for the purpose of exemplifying certain techniques implemented for the purpose of testing and validating the various embodiments of the invention described herein.

As in FIG. 4, the process of FIG. 5A is applied to dual axis accelerometry data 502 representative of multiple swallowing events; the data in this example, however, is explicitly labeled as data acquired along the anterior-posterior axis and superior-inferior axes, respectively. Clearly, previously segmented and/or individually recorded data sets may also be utilized in this context, bypassing segmentation step 506 described below.

A data preprocessing step 504 is once again applied to the accelerometry data, consisting in this example, of an inverse filter, which may include various low-pass, band-pass and/or high-pass filters, followed by signal amplification (e.g. in the example below, accelerometry data was band-pass filtered 0.1 Hz to 3 kHz with 10× amplification). A denoising subroutine is then applied to the inverse filtered data, which may consist, in one example, of processing signal wavelets and iterating to find a minimum mean square error, for example as described in co-pending application Ser. No. 12/819,216, the entire contents of which are incorporated herein by reference. It will be appreciated that various optimization schemes may be implemented to find such minimum value, as can alternative denoising subroutines to achieve similar results in accordance with different embodiments of the invention.

In one example, the preprocessing module may further comprise a subroutine for the removal of candidate movement artifacts from the data, for example, in relation to a candidate's head movement. In one such example, a splines-based subroutine may be implemented to achieve satisfactory artifact removal; however, other techniques may also be applied to achieve similar results. Other signal artifacts, such as vocalization, blood flow, and the like, may also be removed from acquired signals as necessary or applicable, in accordance with different embodiments of the invention.

Upon completion of the data preprocessing step 504, which may involve different levels of complexity depending on the quality and reliability of acquired data, and other such parameters, the data is then manually or automatically segmented (step 506) for event-specific processing, as described above. Again, it will be appreciated that data segmentation may be implemented prior to preprocessing, or again, avoided entirely where event-specific data sets are acquired independently.

In this embodiment, the event-specific data is processed through a feature extraction module 508, which consists of calculating one or more time-frequency domain features for each axis-specific data set. In this particular example, the feature extraction module 508 calculates the log-energy of each level of an 18 level sym8 wavelet decomposition of the A-P data, and the entropy of each level of a 12 level sym8 wavelet decomposition of the S-I data. It will be appreciated that alternative combinations of extracted features may be considered herein without departing from the general scope and nature of the present disclosure. Namely, while different features are extracted for each axis-specific data set, it will be appreciated that the same features may be extracted in each case, or again, that multiple features may be extracted from each set, and that, in different combinations. Furthermore, other features may be considered for feature extraction, for example, including one or more time, frequency and/or time-frequency domain features (e.g. mean, variance, center frequency, etc.).

Upon feature extraction, an optional feature reduction module 510 is then implemented to further process the data for effective classification. For example, the feature reduction module may be configured to select a subset of the extracted features for classification, for instance based on the previous analysis of similar extracted feature sets derived during classifier training and/or calibration. For example, in one embodiment, the most prominent features or feature components/levels extracted from the classifier training data set are retained as most likely to provide classifiable results when applied to new test data, and are thus selected to define a reduced feature set for training the classifier and ultimately enabling classification. For instance, in the context of wavelet decompositions, or other such signal decompositions, techniques such as linear discriminant analysis, principle component analysis or other such techniques effectively implemented to qualify a quantity and/or quality of information available from a given decomposition level, may be used on the training data set to preselect feature components or levels most likely to provide the highest level of usable information in classifying newly acquired signals. Such preselected feature components/levels can then be used to train the classifier for subsequent classifications. Ultimately, these preselected features can be used in characterizing the classification criteria for subsequent classifications.

Accordingly, where the device has been configured to operate from a reduced feature set, such as described above, this reduced feature set will be characterized by a predefined feature subset or feature reduction criteria that resulted from the previous implementation of a feature reduction technique on the classifier training data set. Newly acquired data will thus proceed through the various pre-processing and segmentation steps described above (steps 504, 506), the various swallowing events so identified then processed for feature extraction at step 508 (e.g. full feature set), and those features corresponding with the preselected subset retained at step 510 for classification at step 512.

While the above exemplary approach contemplates a discrete selection of the most prominent features, other techniques may also readily apply. For example, in some embodiments, the results of the feature reduction process may rather be manifested in a weighted series or vector for association with the extracted feature set in assigning a particular weight or level of significance to each extracted feature component or level during the classification process. This particular approach was taken in achieving the results provided by the Example below. In particular, selection of the most prominent feature components to be used for classification in this example was implemented via linear discriminant analysis (LDA) on the classifier training data set. Namely, the resulting extracted and reduced feature for each axis was taken as the weighted sum of the log-energy calculated for each level of the 18-level sym8 wavelet decomposition of the A-P axis data, and the weighted sum of the entropy calculated for each level of the 12-level sym8 wavelet decomposition of the S-I data, wherein respective weights for each summation was calculated from LDA of these same features when extracted from the training data set. As validated by the results presented in the below Example, this approach to feature extraction and reduction was effectively used to distinguish safe from potentially unsafe swallows, and efficient from potentially inefficient swallows. Namely, as evidenced by the below results and validation of the above-described technique, the extraction of these selected features from new test data can now be compared to preset classification criteria established as a function of these same selected features as previously extracted and reduced from an adequate training data set, to classify the new test data as representative of a normal vs. impaired swallow (e.g. safe vs. unsafe swallows and/or efficient vs. inefficient swallows).

As will be appreciated by the skilled artisan, other feature sets, such as frequency, time and/or time-frequency domain features, may also be considered to provide similar results. Similarly, while the above provides one example of a selected subset of features identified via an applied feature reduction process, other feature selections based on similar feature reduction techniques (e.g. genetic algorithms, principal component analysis, etc.) and/or identified from a different training data set, may also be considered to provide similar results.

Upon feature reduction, feature classification is implemented by classification module 512, which in this embodiment, implements a discriminant analysis using Mahalanobis distances with stratified covariance estimates to compare the extracted features (or reduced/weighted subset thereof) of acquired swallow-specific data with preset classification criteria so to effectively classify each data set as representative of a normal swallowing event or a potentially impaired swallowing event. As will be appreciated by the skilled artisan, different classification techniques may be implemented in classifying swallowing event data, which may include for example, genetic algorithms, principal component analysis, neural networks, etc.

Figure 9:
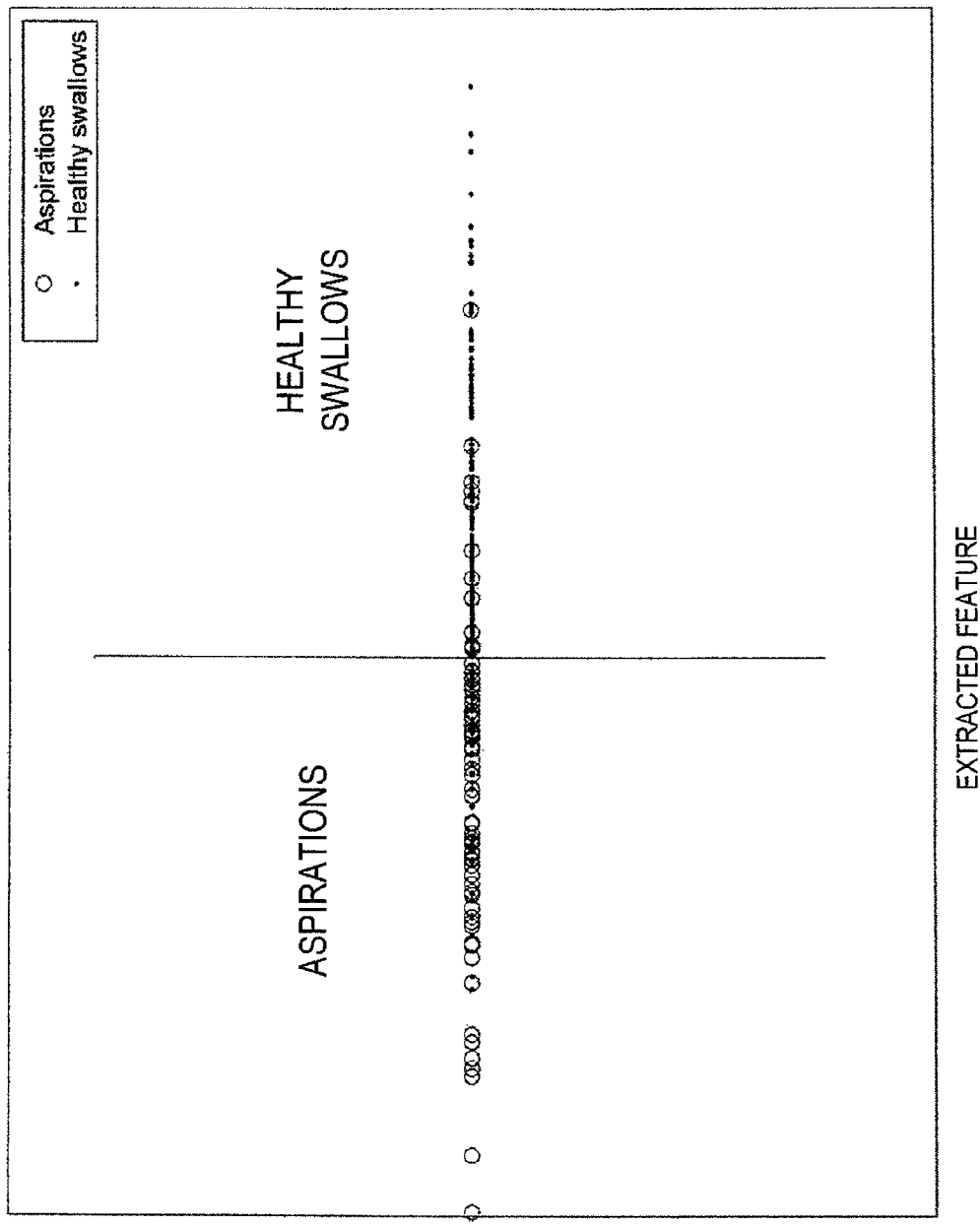
FIG. 9 is a graphical representation of a classification of a training data set, for use in subsequent classifications of test swallowing events as indicative of a healthy swallowing event vs. a possible aspiration event, in accordance with one embodiment of the invention.

In the Example provided below, positive results were achieved via the above-described technique, wherein extracted features were ultimately evaluated as a function of their effective distance from a previously classified training data set representative of healthy and unhealthy swallows. FIG. 9 provides a graphical representation of classification data, wherein healthy and aspiratory swallowing events are delimited by a line in this one-dimensional illustration. In the context of a multidimensional data set, for example where one or more features are extracted for each of the two data axes, a vectorial distance from a pre-classified training data set can be effectively defined to adequately classify new data sets.

Figure 6:
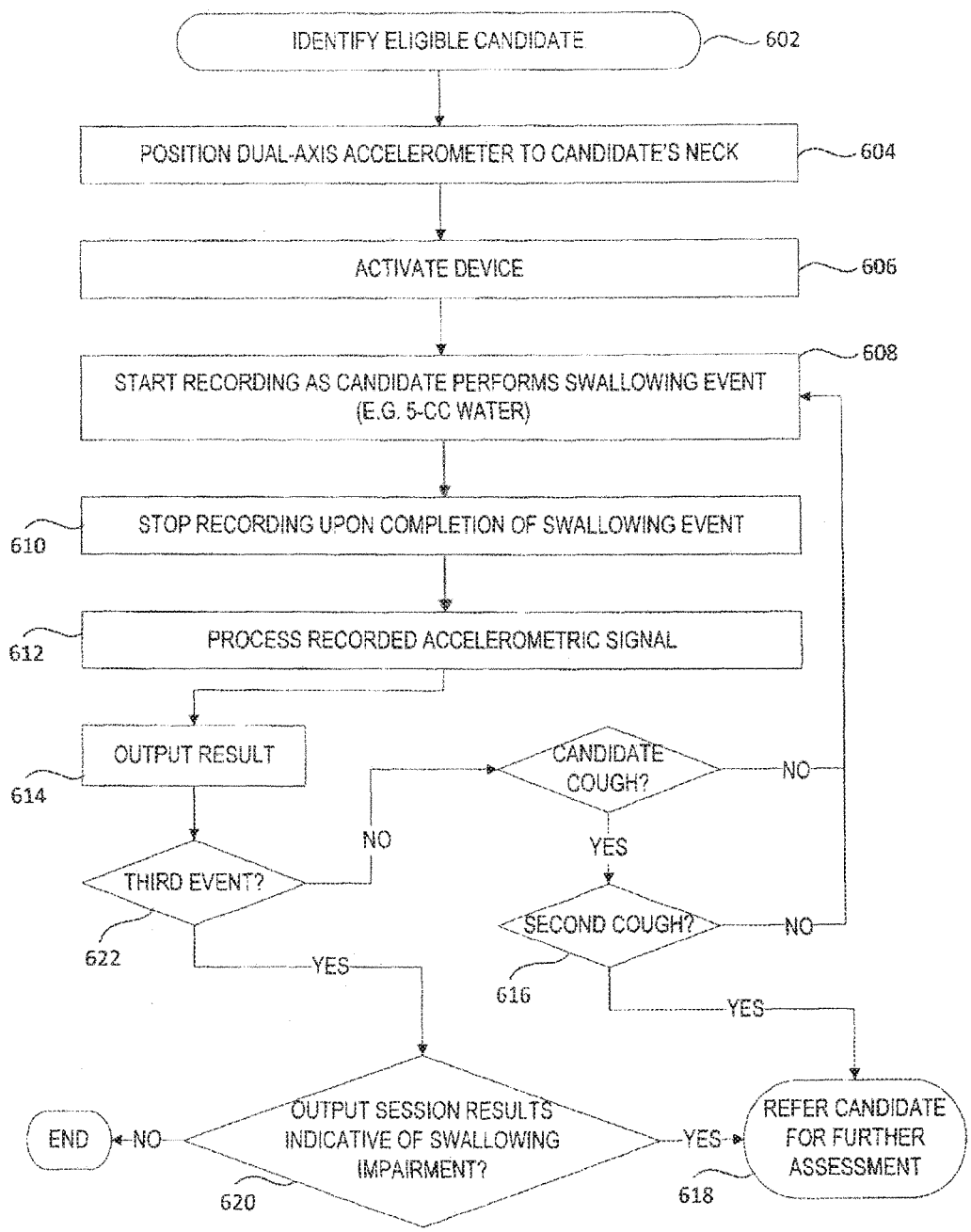
FIG. 6 is a flow chart of a candidate screening and testing protocol for implementation using a swallowing impairment screening device, in accordance with one embodiment of the invention.

In one embodiment, a clinical impairment detection protocol, for example as described below with reference to FIG. 6, is implemented on a swallow-by-swallow basis, whereby a screening/diagnosis with respect to potential aspiration, and/or other such impairments, is executed for each swallowing event independently. In such embodiments, swallowing event data classification is implemented independently for each acquired data set (signal segmentation is also effectively avoided), whereby features extracted from this event-specific data set is classified upon comparison with preset classification criteria established, for example, on the basis of repeated clinical trials and/or device calibration implemented via similar data processing techniques.

For example, in one embodiment, depicted by the dashed-line boxes of FIG. 5A as an optional training/validation subroutine 516, a data set representative of multiple swallows is processed as described above such that each swallow-specific data set ultimately experiences the preprocessing, feature extraction and feature reduction modules described above. The training/validation subroutine 516, however, applies a validation loop to the discriminant analysis based classifier via a leave-one-out validation process, or other such cross-validation processes, which may include, for example, a similar K-fold validation process. Once all events have been classified and validated, output criteria may be generated for future classification without necessarily applying further validation to the classification criteria. Alternatively, routine validation may be implemented to either refine the statistical significance of classification criteria, or again as a measure to accommodate specific equipment and/or protocol changes (e.g. recalibration of specific equipment, for example, upon replacing accelerometer with same or different accelerometer type/model, changing operating conditions, new processing modules such as further preprocessing subroutines, artifact removal, additional feature extraction/reduction, etc.).

Figure 5B:
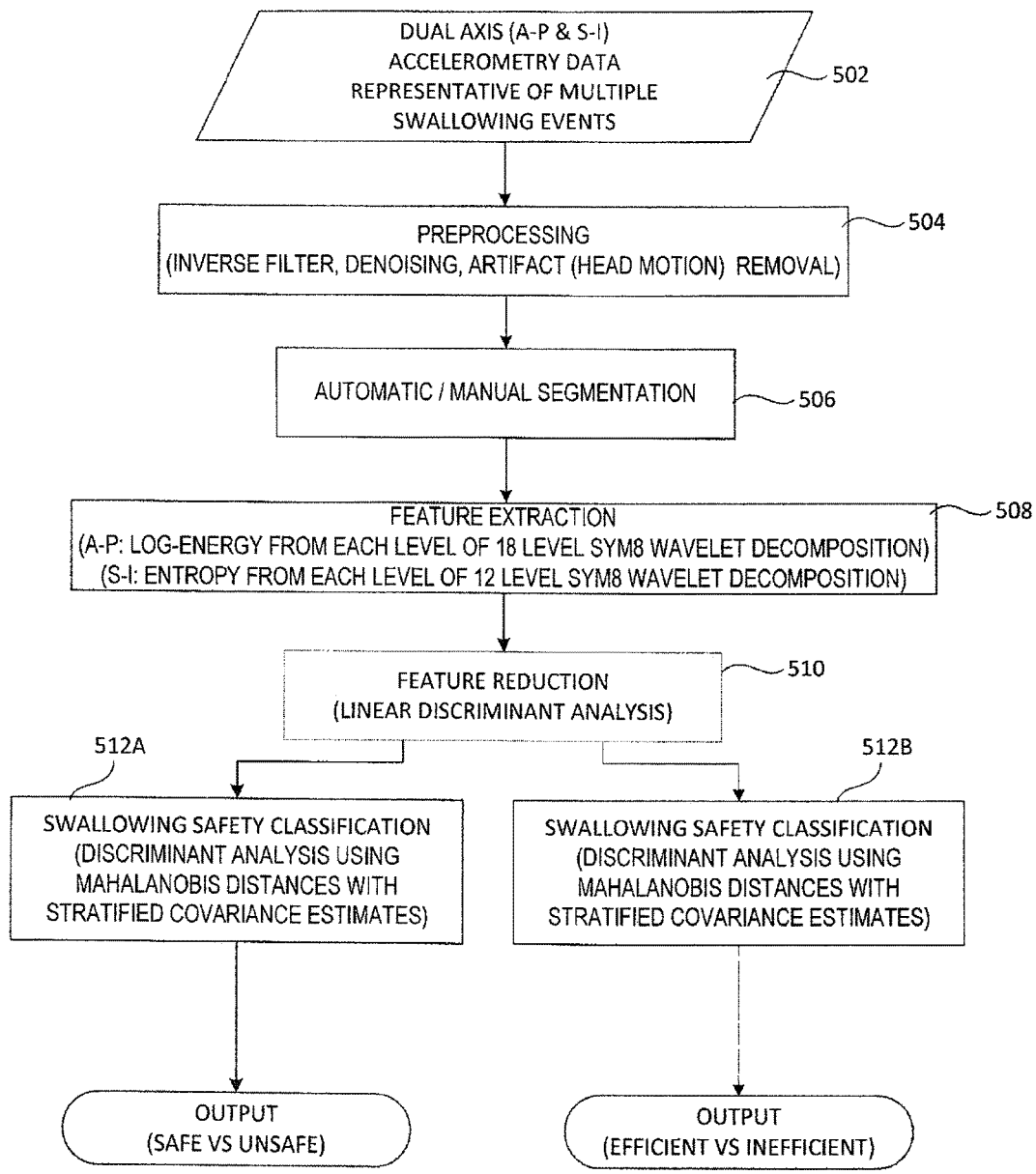
FIG. 5B is a detailed dual axis accelerometry data processing flow diagram for implementation by a swallowing impairment detection device in screening for both swallowing safety and efficiency, in accordance with one embodiment of the invention.

With reference to FIG. 5B, a similar process as described above with reference to FIG. 5A is presented. In this process, steps 502 to 510 are kept substantially unchanged; however, the process proceeds to distinct classification steps 512A and 512B in the classification of the acquired event-specific vibrational data as indicative of safe vs. unsafe swallows, and as indicative of efficiency vs. inefficient swallows. For example the same feature extraction and reduction techniques may be commonly applied prior to the application of the distinctive classifications, which classifications may rely on distinct classification criteria previously defined as a function of respective classifier training. For instance, the same classification technique may be employed, but trained in accordance with distinct parameters, namely based on a known training data set (which may be the same for establishing both sets of classifying criteria) segregated into safe vs. unsafe swallowing events, and efficient vs. inefficient swallowing events, respectively. In such embodiments, the device may thus be configured to perform two distinct classifications in parallel or in sequence, to achieve greater screening accuracy and complexity. It will be appreciated that while the above example considers the implementation of a same feature extraction, reduction and classification technique for both intended classifications, a distinct technique may otherwise be applied to each classification problem, without departing from the general scope and nature of the present disclosure.

With reference to FIG. 6, an exemplary clinical or bedside protocol is provided in implementing a testing or screening sequence for impairment detection via dual-axis accelerometry, with candidates satisfying the following eligibility criteria:

a) patient must be alert and awake;
b) patient must be able to breathe freely on room air (those with tracheostomies or on supplemental oxygen should proceed directly to a full assessment);
c) patient should be able to sit upright with minimal support, and able to hold head upright;
d) patient should be able to follow simple instructions; and
e) patient's mouth should be clean and free of debris before proceeding; dentures may, but do not need to be worn for this test.

As depicted in FIG. 6, upon identifying a patient as an eligible candidate (602), the testing or screening sequence proceeds as follows. At step 604, a dual-axis accelerometer is positioned on the candidates neck (e.g. by way of a strap, elasticized band and/or double-sided adhesive tape), for example in midline, anterior to the cricoid cartilage. At step 606, the device is activated (e.g. device turned on, application running on a portable screening device activated, and/or application set to initiate new screening session initiated). At step 608, and generally once the candidate has been provided with a given quantity of a substance to be swallowed as a first swallowing event (e.g. a 5-cc cup of water), recording is started, thus allowing recordal of respective accelerometric signals for each axis and corresponding to the candidate's first swallowing event (e.g. via a device push button or a virtual button rendered on a graphical user interface of the device). Upon completion of the swallowing event, or where the candidate begins coughing, recording is stopped at step 610 (e.g. upon pushing the same or a distinct physical/virtual button), and the recorded signals automatically processed (step 612) for classification as indicative of a safe vs. unsafe swallow (and/or efficient vs. inefficient swallow). In one embodiment, the graphical user interface of the device is configured to output a result at step 614 for the completed swallowing event, which may be noted manually, or tracked sequentially by the device for each subsequent event. Exemplary outputs may include, but are not limited to, a message such as "No aspiration/residue detected" or "Possible aspiration/residue detected", a colour coded light or indicia to identify a safe swallowing event (e.g. green), possibly unsafe swallowing event (e.g. red), or possibly inefficient swallowing event (e.g. orange), and/or other such display mechanisms. Note that such results may alternatively be recorded automatically by the device to render a consolidated/overall report at the end of the protocol/session, thus further reducing reliability on user intervention.

In this exemplary embodiment, the above steps are repeated for 3 swallowing events, unless coughing is identified during the first two events, at which point, the session is ended after two events at step 616 and the candidate automatically referred to further assessment (e.g. via VFSS) at step 618. Otherwise, overall results may be output at step 620 (e.g. upon pressing an "end session button" or again automatically output upon the device acknowledging at step 622 the completion of the session's prescribed three swallowing events) and, where results are indicative that the candidate may be exhibiting a swallowing impairment (e.g. detection of at least one possibly unsafe or inefficient swallowing event), the candidate is again referred for further assessment at step 618.

It will be appreciated that different embodiments may be configured to provide different levels of information, consistent with the classification techniques employed and level of training implemented in configuring the device. For example, in one embodiment, the device is configured to output an indication as to potential swallowing safety impairment (e.g. healthy swallow vs. possible penetration/aspiration). In another embodiment, the device may be further configured to also output an indication as to potential swallowing efficiency impairment (e.g. absence vs. presence of residue post-swallow). In such embodiments, the device would effectively process the recorded signal based on a dual classification process, namely one trained to identify aspiration risk, and the other to identify swallowing inefficiencies, the combined results thus providing for a more complete dysphagia screening and characterization process, for example.

From the above, it is appreciated that limited training and intervention is required for implementation of the above protocol in assessing aspiration and/or swallowing efficiency risks. Namely, the device considered herein in accordance with different embodiments of the invention allows for the ready assessment, or preassessment (e.g. screening) of potential aspiration/dysphagia candidates, without significant operator intervention, contrary to traditional swallowing impairment detection techniques. Furthermore, and as validated by the results of the specific example described below, the reliability of the results output using this approach, as compared to other approaches, makes for a greater candidate assessment tool resulting in fewer misdiagnoses and/or fewer referral of otherwise healthy patients to further and generally more invasive treatment/testing procedures.

The following provides an example of a swallowing impairment detection system, method and device, in accordance with an embodiment of the invention, validated by the parallel implementation of videofluoroscopic examinations. It will be appreciated by the person of ordinary skill in the art that the following describes an exemplary embodiment of the invention, and is not intended as a limiting disclosure, but rather merely illustrative of one of different possible embodiments of the inventive impairment detection method, system and devices considered within the context of the present disclosure.

EXAMPLE 1

Participants

Participants included 40 adults (20 female; mean age 67), referred for videofluoroscopy to investigate swallowing complaints. Individuals with a history of head and neck cancer, tracheostomy, neurodegenerative disease, gastrointestinal disorders, or head and neck surgery (except routine tonsillectomy or adenoidectomy) were excluded.

Data Collection

Time-linked dual-axis accelerometry signals (Aspirometer) were collected during videofluoroscopy, using a protocol of three sips of thin liquid barium (5 cc each), followed by a cup drinking task.

Swallowing data were collected using a brief screening protocol during a standardized videofluoroscopy examination. In particular, time-linked dual-axis accelerometry signals (Aspirometer) were collected during the videofluoroscopic examination, using a protocol of three 5-cc swallows of thin liquid barium (Polibar thin liquid barium suspension (BraccoImaging), diluted to 40% w/v density with water) followed by a cup drinking task. The lateral view videofluoroscopy recording was captured and time-stamped at 30 frames per second in Labview software (National Instruments). Concurrent cervical accelerometry signals were collected via a dual-axis accelerometer (Analog Devices, ADXL322), attached to the participant's neck in midline, anterior to the cricoid cartilage, using double-sided adhesive tape. The anterior-posterior (A-P) and superior-inferior (S-I) accelerometry axes were oriented so that the anterior and superior directions corresponded to positive signal polarities.

The videofluoroscopy recordings were spliced into individual swallow clips capturing the interval between the arrival of the bolus head at the mandibular ramus, and the minimum hyoid position following each swallow. Spontaneous clean-up swallows, following the initial swallow of each bolus, were spliced into separate clips, beginning at the lowest hyoid position before each new swallow event. The cropped recordings were then arranged in random order and reviewed by two speech-language pathologists, blinded to patient identity. The 8-point Penetration-Aspiration Scale was used to rate the occurrence of airway invasion and ratings were subsequently collapsed to a binary scale ($\leq 2$ vs. $\geq 3$), distinguishing transient entry of material into the laryngeal vestibule with subsequent clearance (safe), from deeper entry of material without clearance (unsafe). For simplicity's sake, we will refer to the group without airway clearance as "aspirators", although it is recognized that this group included both those with penetration and with aspiration proper.

The signal processing steps applied to the accelerometry data are substantially as summarized in FIG. 5A. The signal was filtered and amplified, (e.g. band-pass filtered 0.1 Hz to 3 kHz with 10× amplification, then sampled at 10 kHz and stored on an associated computing device with time index corresponding to associated videofluoroscopy timestamps. Inverse filters were then used for pre-processing followed by denoising using a discrete Meyer wavelet transform with soft thresholding. In this example, a spline-based approach was also used to then remove low frequency components associated with head motions. Other filters may also be applied to further reduce noise or artifacts in the signal, as will be readily appreciated by the skilled artisan.

In a first example, the accelerometric signals were then manually segmented into swallow clips based on the locations of the onsets and offsets identified in the videofluoroscopy recordings. In the absence of concurrent videofluoroscopic recordings, namely consistent with the implementation of a self-standing aspirometer based on dual-axis accelerometer, manual segmentation may otherwise be implemented via visual inspection of the acquired signal, or again via individual swallow-synchronized signal recordings.

In another example, accelerometric signals were automatically segmented, for example as described in co-pending United States Patent Application Publication No. 2010/0160833, where candidate peaks in the signal are automatically identified as representative of swallows. This automated segmentation approach was originally developed using videofluoroscopically confirmed time windows capturing the events between bolus entry into the pharynx and the return of the hyolaryngeal complex to a resting position after the swallow, and has been demonstrated to effectively find peaks in the preprocessed signal. As such, the system is capable of subdividing the physiological sequence of ingestion for a single bolus into sub-swallows in the event that a person uses multiple swallows for a single bolus. The boundaries of each subswallow peak can thus be derived automatically from the signal, when appropriate, if using such an automated segmentation module.

From the segmented swallows, axis-specific features were extracted, for instance as described above with reference to FIG. 5A. In this particular example, and as described above, extracted features included the log-energy from each level of an 18 level sym8 wavelet decomposition for A-P axis data, and the entropy from each level of a 12 level sym8 wavelet decomposition for S-I axis data. Feature reduction using linear discriminant analysis was then implemented to apply respective weights to each level in identifying prominent features of the available data set, which weighted features were then used as a metric for classification using Mahalanobis distances with stratified covariance estimates to provide the below classification results. An iterative process of leave-one-out classification was used to train the classifier given the available data, which is akin to a K-fold cross-validation, using a single observation from the original sample as validation data, and the remaining observations as training data, with repetition, such that each observation is used once as validation data.

Results

Complete videofluoroscopic and accelerometry data were available for 37 of the 40 participants in this study. In 3 cases, videofluoroscopy image quality issues such as an obstructed view of the airway by the shoulder shadow precluded verification of the accelerometry classifier result. The final dataset included 261 swallowing events, with 31% (80 swallows) displaying penetration-aspiration scale scores of 3 or greater. When the data for all swallows by each participant were considered in aggregate, aspiration was found to occur in 35% (n=13) of the 37 participants. The results of the utility analysis for the detection of impaired swallowing safety and efficiency by the accelerometry classifier are shown at the bolus level (each sip or mouthful) as well as at the subswallow and participant levels in FIG. 7. Greater detail regarding the detection of penetration-aspiration at the subswallow and participant levels is shown in FIG. 8.

The initial episodes of aspiration for the 13 aspirating participants were distributed across the tasks in the protocol. For the 4 participants who showed their initial episode of aspiration on the first teaspoon of thin liquid in the protocol, aspiration was correctly identified by the classifier in all cases. For the 6 participants whose initial episodes of aspiration commenced on either the second and third teaspoons of thin liquid, classifier sensitivity was 66% and 50%, respectively. The classifier performed with 100% sensitivity in capturing two episodes of aspiration that occurred for the first time during the cup drinking task.

In this example, dual-axis cervical accelerometry signals were recorded during videofluoroscopy in adults suspected of having dysphagia. In a related analysis, clinicians were asked to review movies showing the heads and faces of these same participants performing the swallow screening tasks, and to record the occurrence of clinical signs of swallowing difficulty. The presence of abnormal clinical signs, judged by both registered nurses and speech-language pathologists, was found to have 54-75% sensitivity for detecting aspiration, on a participant-by-participant basis. These clinical judges were found to err on the side of over-identifying possible aspiration, with specificities ranging from 25-44%. These results were similar in sensitivity, and slightly worse in specificity to those found in another study for perceptual judgments of 20 stethoscope-recorded swallowing sound clips by experienced speech-language pathologists (62% sensitivity, 66% specificity). The results of this example show that dual-axis cervical accelerometry signal, when processed through a classifier, as considered herein within the context of the present disclosure, performs better, with improved sensitivity (85%) and specificity (77%) for aspiration detection, compared to perceptual judgments by clinicians, at the level of the single swallow. Specificity dropped slightly to 54% when the combined results of all swallows were considered for each individual, but sensitivity and negative predictive value rose to 100%, reflecting a zero false negative rate.

Ultimately, the classification method and device considered in this example succeeded in effectively distinguishing safe from unsafe swallows at the level of the single bolus with 90% sensitivity and 77% specificity. When all four of the swallowing tasks performed by each patient were considered in aggregate, sensitivity for the detection of aspiration (i.e. anywhere in the protocol) improved to 100%, but specificity fell to 54%. Furthermore, the classification method employed succeeded in discriminating swallows displaying post-swallow residue occupying at least 25% of the available space in the pharyngeal recesses (valleculae and pyriform sinuses) with 81% sensitivity and 76% specificity.

Other studies have suggested that the opportunity to catch aspiration increases with additional water swallow trials. In this example, however, the screening protocol involved a series of only 3 teaspoon-sized boluses of thin liquid, followed by a cup drinking task. While it is not known with absolute certainly how many of the non-aspirating participants tested in this example might have aspirated, given additional trials, the proposed classifier was able to correctly detect aspiration on either its first or second occurrence in all 13 participants who showed aspiration. In swallowing assessment, it is generally accepted that 3 repetitions of a task provide a representative sample of patient performance. In this study, there were only 2 of the 13 aspirating participants who showed their first episodes of aspiration on the final (i.e., fourth) cup drinking task. These results support the use of the brief thin liquid swallowing protocol used in this example, as a valid and adequate method for identifying aspiration risk, but also point to the possible benefit, while optional, of including a larger volume challenge, which may provoke aspiration in some patients who appear safe on smaller controlled volumes.

It will be appreciated by the person of ordinary skill in the art that while the above presents an exemplary protocol for detecting swallowing impairment, and particularly aspiration, such protocol may be varied to achieve similar effects and results depending on the type of candidate being considered and the level of accuracy sought after. For example, in some examples, a protocol may be devised for detecting aspiration in candidates having a reduced level of consciousness, which would thus preclude the administration of water swallowing tasks, but may nonetheless benefit from the accelerometry data acquisition and processing techniques described above. Furthermore, it will be appreciated that the above described technique may be considered in the context of candidates having suffered a stroke or other such medical traumas, or in otherwise healthy candidates. Also, the proposed techniques may be applicable in the detection of aspiration below the true vocal folds (e.g. ignoring penetration), to a broader diagnosis of dysphagia, encompassing penetration, aspiration and other abnormalities of oropharyngeal swallowing physiology.

In any event, the above-proposed techniques and devices may be considered in providing a substantial non-invasive approach to swallowing impairment detection, and that, in comparison with other techniques, with a reduced false positive rate and higher specificity. As will be appreciated by the skilled artisan, a reduced false positive rate may be beneficial to prospective candidates who, upon improper diagnosis, may be subjected to the overzealous use of interventions that turn out to be unnecessary. For example, in the case of swallow screening, the recognition of aspiration risk becomes the reason for implementing severe dietary restrictions (e.g. nothing by mouth) until further assessment results become available. As a means to reduce the likelihood of such unnecessary restrictions, the accelerometry classifier used in this example showed 77% specificity and 23% false positives at the level of a single bolus, and 54% specificity with 46% false positives across the entire protocol of 4 thin liquid swallowing tasks.

This example shows that dual-axis cervical accelerometry, as discussed and considered in accordance with different embodiments of the invention, provides a reasonable alternative to known techniques in providing a substantially noninvasive technique for accurately detecting swallowing impairments, as evidenced by the results of the above-described example evaluating thin liquid aspiration and efficiency risks during a brief water swallow screening protocol. As evidenced by the results of this example, the signal/data processing techniques discussed herein can achieve swallowing impairment detection rates that surpass clinical judges in accuracy, which promotes the use of such techniques in early swallowing impairment identification initiatives without requiring extensive nurse training, competency-maintenance and staffing resources.

While the present disclosure describes various exemplary embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A device for use in identifying a possible swallowing impairment in a candidate during execution of a swallowing event, the device comprising:
   a dual axis accelerometer configured for alignment along an anterior-posterior (A-P) axis and a superior-inferior (S-I) axis of the candidate's throat and to acquire axis-specific vibrational data representative of the swallowing event; and
   a processing module that is a local or remote computing device operatively coupled to the accelerometer, the processing module configured for processing the axis-specific data to (i) extract therefrom distinct axis-specific features representative of the swallowing event, the distinct axis-specific features comprising a log energy of vibrational data acquired along the A-P axis and absent a log energy of vibrational data acquired along the S-I axis, the distinct axis-specific features further comprising an entropy of vibrational data acquired along the S-I axis and absent an entropy of vibrational data acquired along the A-P axis, (ii) perform a comparison of the distinct axis-specific features against preset classification criteria defined for each of swallowing safety and swallowing efficiency, and (iii) classify the vibrational data as one of a first classification or a second classification based on the comparison of the distinct axis-specific features against the preset classification criteria defined for each of the swallowing safety and the swallowing efficiency.

2. The device of claim 1, wherein the second classification is indicative of at least one of a swallowing safety impairment or a swallowing efficiency impairment.

3. The device of claim 1, wherein the second classification is indicative of penetration or aspiration, the processing module configured to further classify the swallowing event as indicative of one of a first event and a second event based on the comparison of the distinct axis-specific features against the preset classification criteria defined for each of the swallowing safety and the swallowing efficiency.

4. The device of claim 1, wherein the log energy of the vibrational data acquired along the A-P axis data comprises a log energy of each level of an 18 level sym8 wavelet decomposition of the vibrational data acquired along the A-P axis, and the entropy of the vibrational data acquired along the S-I axis data comprises an entropy of each level of a 12 level sym8 wavelet decomposition of the vibrational data acquired along the S-I axis.

5. The device of claim 4, wherein the distinct axis-specific features comprise a weighted sum of the log energy of each level of the 18 level sym8 wavelet decomposition of the vibrational data acquired along the A-P axis, and a weighted sum of the entropy of each level of the 12 level sym8 wavelet decomposition of the vibrational data acquired along the S-I axis, wherein weights in each of the weighted sums are defined by preset feature reduction parameters.

6. The device of claim 1, wherein the preset classification criteria are defined by features previously extracted and classified from a known training data set.

7. The device of claim 1, wherein the distinct axis-specific features are classified as a function of distances of values of the distinct axis-specific features from values of the preset classification criteria.

8. The device of claim 7, wherein the distinct axis-specific features are classified as the function of the distances via discriminant analysis using Mahalanobis distances with stratified covariance estimates.

9. The device of claim 1, wherein the classification of the vibrational data as one of the first classification or the second classification comprises identifying, based on preset feature reduction parameters, predominant components of the distinct axis-specific features and the classification of the vibrational data is based on the distinct axis-specific features and the predominant components thereof.

10. The device of claim 1, configured to identify the second classification during execution of multiple successive swallowing events, by the processing module classifying the vibrational data acquired in respect of each of the successive swallowing events as indicative of one of the first classification or the second classification.

11. The device of claim 10, wherein the processing module is configured for automatically segmenting the vibrational data acquired in respect of each of the successive swallowing events for independent processing and classification.

12. The device of claim 10, comprising a user interface for selectively segmenting the vibrational data acquired in respect of each of the successive swallowing events for independent processing and classification.

13. The device of claim 10, comprising a display, the processing module further configured to process the vibrational data acquired in respect of each of the successive swallowing events, and output the one of the first classification or the second classification on the display in accordance with a preset swallowing impairment assessment protocol.

14. The device of claim 1, comprising a pressure sensor or pressure sensitive film positioned so to monitor a pressure applied by the accelerometer when positioned on the candidate's throat to increase data acquisition accuracy.

15. A method for classifying cervical dual-axis accelerometry data acquired in respect of a candidate swallowing event to identify a possible swallowing impairment, the method comprising:
  receiving as input axis-specific vibrational data from an anterior-posterior (A-P) axis and a superior-inferior (S-I) axis and representative of the swallowing event, a processing module that is a local or remote computing device operatively coupled to a dual axis accelerometer receives the axis-specific vibrational data from the dual axis accelerometer;
  extracting distinct axis-specific features representative of the swallowing event from the axis-specific vibrational data, the processing module extracts the distinct axis-specific features, the distinct axis-specific features comprising a log energy of vibrational data acquired along the A-P axis and absent a log energy of vibrational data acquired along the S-I axis, the distinct axis-specific features further comprising an entropy of vibrational data acquired along the S-I axis and absent an entropy of vibrational data acquired along the A-P axis;
  comparing the distinct axis-specific features with preset classification criteria defined as a function of the distinct axis-specific features, the processing module compares the distinct axis-specific features with the preset classification criteria; and
  outputting, based on the comparing step, classification of the vibrational data as one of a first classification or a second classification, the processing module outputs the classification.

16. The method of claim 15, wherein the second classification is indicative of one or more of unsafe swallowing and inefficient swallowing.

17. The method of claim 15, wherein the second classification is indicative of at least one of a penetration risk and an aspiration risk.

18. The method of claim 15, wherein the log energy of the vibrational data acquired along of the A-P axis comprises a log energy of each level of an 18 level sym8 wavelet decomposition of the vibrational data acquired along the A-P axis, and the entropy of the S-I axis data comprises an entropy of each level of a 12 level sym8 wavelet decomposition of the vibrational data acquired along the S-I axis.

19. The method of claim 18, comprising reducing the distinct axis-specific features by associating respective weights to each level of the 18 level sym8 wavelet decomposition of the vibrational data acquired along the A-P axis and each level of the 12 level sym8 wavelet decomposition of the vibrational data acquired along the S-I axis.

20. The method of claim 15, wherein the comparing step comprises calculating distances of values of the distinct axis-specific features from values of the preset classification criteria and selecting a most likely classification as a function of the distances.

21. The method of claim 20, wherein the calculating of the distances comprises performing a discriminant analysis of the distinct axis-specific features using Mahalanobis distances with stratified covariance estimates.

22. The method of claim 15, wherein the receiving step comprises receiving as input axis-specific vibrational data representative of successive swallowing events, the method comprising segmenting the vibrational data into event-specific data, and repeating the extracting and comparing steps for each of the event-specific data.

23. The method of claim 22, wherein the segmenting step is implemented automatically.

24. The method of claim 22, wherein the outputting step comprises outputting the classification of the vibrational data as one of the first classification or the second classification in accordance with a preset swallowing impairment assessment protocol.

25. A method for identifying a possible swallowing impairment in a candidate via execution of one or more preset swallowing events, comprising:
  recording dual-axis vibrational data along an anterior-posterior (A-P) axis and a superior-inferior (S-I) axis, the dual-axis vibrational data is representative of the one or more preset swallowing events, a processing module that is a local or remote computing device operatively coupled to a dual axis accelerometer records the dual-axis vibrational data from the dual axis accelerometer;
  extracting distinct axis-specific time-frequency domain features from the dual-axis vibrational data, the processing module extracts the distinct axis-specific time-frequency domain features, the distinct axis-specific time-frequency domain features comprising a log energy of vibrational data acquired along the A-P axis and absent a log energy of vibrational data acquired along the S-I axis, the distinct axis-specific time-frequency domain features further comprising an entropy of vibrational data acquired along the S-I axis and absent an entropy of vibrational data acquired along the A-P axis; and
  classifying the distinct axis-specific time-frequency domain features as one of a first classification or a second classification, the processing module classifies the distinct axis-specific time-frequency domain features.

26. The method of claim 25, further comprising, during the recording step, having the candidate execute the one or more swallowing events.

27. The method of claim 25, comprising, for execution of two or more preset swallowing events, selectively recording the dual-axis vibrational data for each event independently to provide event-specific data, and implementing the extracting and classifying steps on the event-specific data for each of the events.

28. The method of claim 27, comprising identifying the candidate as exhibiting a potential swallowing impairment upon classifying the distinct axis-specific time-frequency domain features of at least one of the two or more preset swallowing events as indicative of possible swallowing impairment.

29. The method of claim 28, wherein the potential swallowing impairment comprises unsafe swallowing, the method comprising identifying the candidate as a low aspiration risk candidate upon classifying at least three successive swallowing events as not indicative of possible swallowing impairment.

30. The method of claim 25, comprising, for execution of two or more preset swallowing events, successively recording the dual-axis vibrational data for each of the events, and comprising automatically segmenting the successively recorded data to provide event-specific data, and implementing the extracting and classifying steps on the event-specific data for each of the events.

31. The method of claim 25, wherein the second classification is indicative of at least one impairment selected from the group consisting of penetration, aspiration, unsafe swallowing and inefficient swallowing.

32. The method of claim 25, wherein the second classification is indicative of one or more of unsafe swallowing and inefficient swallowing, the classifying step comprising comparing the distinct axis-specific time-frequency domain features against respective preset classification criteria defined for each of swallowing safety and swallowing efficiency.

33. The method of claim 25, comprising testing a dual-axis vibrational data quality for consistency with preset quality characteristics.

\* \* \* \* \*